US012778596B2

(12) United States Patent
Shamaei et al.

(10) Patent No.: US 12,778,596 B2
(45) Date of Patent: Nov. 3, 2026

(54) OPTIMIZED CUTTING TOOL PATHS FOR ROBOTIC TOTAL KNEE ARTHROPLASTY RESECTION SYSTEMS AND METHODS

(71) Applicant: Monogram Technologies Inc., Austin, TX (US)

(72) Inventors: Kamran Shamaei, Austin, TX (US); Sanath Vurelli, Round Rock, TX (US)

(73) Assignee: Monogram Technologies Inc., Austin, TX (US)

( * ) Notice: Subject to any disclaimer, the term of this patent is extended or adjusted under 35 U.S.C. 154(b) by 121 days.

(21) Appl. No.: 18/780,645

(22) Filed: Jul. 23, 2024

(65) Prior Publication Data

US 2024/0382212 A1 Nov. 21, 2024

Related U.S. Application Data

(63) Continuation of application No. PCT/US2023/061151, filed on Jan. 24, 2023.

(Continued)

(51) Int. Cl.

*A61B 34/30* (2016.01)
*A61B 17/14* (2006.01)
*A61B 17/15* (2006.01)

(52) U.S. Cl.

CPC .......... *A61B 17/142* (2016.11); *A61B 17/155* (2013.01); *A61B 17/157* (2013.01); *A61B 34/30* (2016.02)

(58) Field of Classification Search

CPC ..... A61B 17/155; A61B 17/157; A61B 34/32; A61B 17/142; A61B 2034/107

See application file for complete search history.

(56) References Cited

U.S. PATENT DOCUMENTS 5,710,870 A * 1/1998 Ohm ........................ B25J 19/02 700/262
8,560,047 B2 10/2013 Haider et al.

(Continued)

FOREIGN PATENT DOCUMENTS

CA 3248842 A1 7/2023
EP 4468988 A1 12/2024

(Continued)

OTHER PUBLICATIONS

International Search Report and Written Opinion of the International Search Authority, International Application No. PCT/US2023/061151, dated Jun. 2, 2023, 15 pages.

(Continued)

*Primary Examiner* — David W Bates
(74) *Attorney, Agent, or Firm* — SCHWEGMAN LUNDBERG & WOESSNER, P.A.

(57) ABSTRACT

Active robotic systems and methods for proximal tibia and/or a distal femur resections via a sagittal cutting blade to facilitate implantation of a total knee arthroplasty prosthesis. The systems include an articulated arm, a sagittal cutting blade defining a cutting edge that is configured to cut while being oscillated, and an end effector coupled to an end arm segment of the articulated arm including a powered drive portion that oscillates the sagittal cutting blade. The system is configured to autonomously adjust the relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of the proximal tibia and/or a distal femur of a patient.

51 Claims, 11 Drawing Sheets

Related U.S. Application Data

(60) Provisional application No. 63/302,527, filed on Jan. 24, 2022.

(56) References Cited

U.S. PATENT DOCUMENTS

| | | | | |
|---|---|---|---|---|
| 8,936,596 | B2 * | 1/2015 | Mittelstadt | G16H 20/40 606/86 R |
| 9,119,655 | B2 * | 9/2015 | Bowling | A61B 34/10 |
| 10,888,337 | B2 | 1/2021 | Shen et al. | |
| 11,564,749 | B2 * | 1/2023 | Becker | A61B 34/30 |
| 11,607,229 | B2 * | 3/2023 | Lavallee | A61F 2/38 |
| 11,864,852 | B2 * | 1/2024 | Moctezuma de la Barrera | A61B 17/1626 |
| 12,035,921 | B2 * | 7/2024 | Kang | A61B 17/14 |
| 2013/0035690 | A1 * | 2/2013 | Mittelstadt | G16H 50/50 382/128 |
| 2014/0039517 | A1 * | 2/2014 | Bowling | A61B 34/74 606/130 |
| 2016/0038291 | A1 * | 2/2016 | Netravali | A61F 2/30942 606/86 R |
| 2016/0206375 | A1 * | 7/2016 | Abbasi | A61B 34/10 |
| 2016/0296296 | A1 * | 10/2016 | Bowling | A61B 34/30 |
| 2016/0338782 | A1 * | 11/2016 | Bowling | A61B 17/1675 |
| 2016/0343273 | A1 * | 11/2016 | Stuart | A61B 34/30 |
| 2018/0353253 | A1 | 12/2018 | Bowling | |
| 2019/0083109 | A1 * | 3/2019 | Steger | A61B 34/10 |
| 2019/0083191 | A1 * | 3/2019 | Gilhooley | A61B 34/30 |
| 2019/0142520 | A1 * | 5/2019 | VanDyken | A61B 90/37 606/1 |
| 2020/0297440 | A1 * | 9/2020 | Forstein | A61G 13/0063 |
| 2021/0093396 | A1 * | 4/2021 | Chappuis | A61B 34/76 |
| 2021/0100629 | A1 | 4/2021 | Urvoy et al. | |
| 2021/0106342 | A1 | 4/2021 | Blackwell | |
| 2021/0353311 | A1 | 11/2021 | Lavallee et al. | |
| 2022/0047329 | A1 * | 2/2022 | Lavallee | A61B 17/00 |
| 2022/0071720 | A1 * | 3/2022 | Sexson | A61B 90/361 |
| 2022/0133331 | A1 * | 5/2022 | Abbasi | B25J 9/1689 606/82 |
| 2025/0049505 | A1 * | 2/2025 | Wolfson | A61B 17/155 |

FOREIGN PATENT DOCUMENTS

| | | | |
|---|---|---|---|
| JP | 2025504892 | A | 2/2025 |
| KR | 20240163063 | A | 11/2024 |
| WO | WO-2019055904 | A1 | 3/2019 |
| WO | 2020236937 | | 11/2020 |
| WO | WO-2023141644 | A2 | 7/2023 |
| WO | WO-2023141649 | A1 | 7/2023 |

OTHER PUBLICATIONS

"European Application Serial No. 23744013.6, Extended European Search Report mailed Dec. 12, 2025", 13 pgs.

"European Application Serial No. 23744013.6, Response to Communication pursuant to Rules 161(2) and 162 EPC filed Mar. 6, 2025", 22 pgs.

"International Application Serial No. PCT/US2023/061151, International Preliminary Report on Patentability mailed Aug. 8, 2024", 6 pgs.

* cited by examiner

OPTIMIZED CUTTING TOOL PATHS FOR ROBOTIC TOTAL KNEE ARTHROPLASTY RESECTION SYSTEMS AND METHODS

CROSS-REFERENCE TO RELATED APPLICATION

The present application is a bypass continuation of International Application No. PCT/US2023/061151, entitled Optimized Cutting Tool Paths for Robotic Total Knee Arthroplasty Resection Systems and Methods, filed on Jan. 24, 2023, which perfects and claims priority benefit of U.S. Provisional Application No. 63/302,527, entitled Optimized Cutting Tool Paths for Robotic Total Knee Arthroplasty Resection Systems and Methods, filed on Jan. 24, 2022, the entireties of which are expressly incorporated herein by reference.

FIELD OF THE DISCLOSURE

The following disclosure relates generally to optimized robotic total knee arthroplasty resection cut methods and systems. More particularly, the following disclosure relates to optimized robotic resection cut path trajectory methods and systems for total knee arthroplasty.

BACKGROUND

Joint arthroplasty is a well-known surgical procedure by which a diseased and/or damaged natural joint is replaced by a prosthetic joint. A total knee arthroplasty (TKA) is an orthopedic surgery procedure in which a diseased and/or damaged knee joint is replaced with a prosthesis.

The most widely-used type of knee prosthesis for implantation into a patient during a TKA procedure includes a femoral component that attaches to the distal femur, a tibial component (or tray) that attaches to the proximal tibia, and an insert (also called a bearing or an inlay) that fits between the femoral and tibial components. To accommodate the implantation of the femoral component and the tibial component of a TKA prosthesis into/onto a patient's femur and tibia, respectively, portions of the patient's femur and tibia are typically resected.

As shown in FIG. 1, TKA generally consists of seven planar resections: a tibial cut on the proximal tibia, a distal femur cut, an anterior femur cut, posterior femur (or condyle) cut, a first chamfer cut extending between the anterior femur cut and the distal femur cut, a second cut extending between the posterior femur cut and the distal femur cut, and patella cut. The substantially planar surfaces on the proximal tibia and the distal femur created by the above-noted resections, as shown in FIG. 1, are preferably cooperatively configured to engage with corresponding engagement surfaces of the tibial component and the femoral component, respectively, of the knee prosthesis.

The resections of the proximal tibia and the distal femur for TKA may be made via a saw blade, such as a sagittal saw blade configured to cut bone, cartilage and/or other tissues of a patient (e.g., a mammalian patient). Sagittal saws are advantageous as they can cut material, such as bone or other tissue, at greater speeds than other cutting tools, such as rotary cutting tools.

As shown in FIG. 2, a sagittal saw blade 10 typically is a planar saw blade that is longitudinally extended along an axis X-X, with a tang portion at one end, a tip portion comprising a cutting edge 12, and a body portion extending between the tang portion and the tip portion. The cutting edge 12 at the tip portion includes a plurality of cutting teeth (and/or abrasives) arranged laterally (extending across the axis X-X) along the plane of the blade 10 (such as linearly or along an arc with a radius aligned with the axis X-X, for example), and that define the free end (i.e., the axial extent) of the blade 10 at the tip portion.

A sagittal saw blade 10 is configured to effectuate cutting via the cutting edge 12 when the blade 10 is translated/moves in an oscillatory, back-and-forth pattern along an oscillation pathway 17 in the plane in which the blade 10 is aligned, and the blade 10 is translated along a longitudinal/axial cut direction 15 extending from the tang portion to tip portion thereof, as shown in FIG. 2. Consequently, when the sagittal saw blade 10 is actuated by a cutting instrument, the cutting edge 12 must move in a back-and-forth pattern against the material to be cut (e.g., tissue or bone) as the blade 10 is translated longitudinally or axially. As a consequence of the motion along the oscillation pathway 17, and forward pressure and translation along the longitudinal/axial cut direction 15 along a cut path, the teeth of the cutting edge 12 of the sagittal saw blade 10 can cut and separate bone.

Due to the arrangement of the oscillation pathway 17 and the longitudinal/axial cut direction 15, a sagittal cutting blade 10 can only cut when the oscillating teeth move across a material along the oscillation pathway 17. That is, a limitation of sagittal cutting blades 10 is that cuts are only possible by lateral movement of the toothed cutting edge 12 across and against the material (bone), which thereby requires that the sagittal saw blade 10 can be only moved forward along its axis X-X to cut. Thereby, a sagittal cutting blade 10 cannot effectuate side cutting along a lateral direction angled (e.g., extending perpendicular) to the longitudinal axis X-X.

The inherent limitations of the unidirectional cutting capability of sagittal saw blades 10 become pronounced when utilizing such blades 10 in surgical procedures, such as in TKA, due to the practical clinical constraints associated with surgery, such as avoiding critical anatomical structures and cutting within bone boundary constraints, for example. As such, currently, only haptic surgical robots utilize superior sagittal cutting blades 10 in surgical settings, such as in TKA resections.

Haptic robots that rely on a user to provide the gross movement of the sagittal cutting blade 10 in the longitudinal/axial cut direction 15 along a cut path (and typically a drive mechanism that operates the sagittal blade 10 along the oscillation pathway 17). Such haptic current surgical robots are thus configured as hand-guided surgical instruments that power the sagittal cutting blade 10 but, at best, only assist a user in translating the sagittal cutting blades 10 to (and through) a patient. Such haptic surgical robots thereby require a user to physically initiated cutting of bone or other tissue with a sagittal cutting blade 10. Sagittal cutting blade 10 also require a user to manually move and direct the sagittal cutting blade 10 along its cutting pathway through the bone or other tissue (i.e., the robot is not actively executing the cuts). For example, some such haptic surgical robots include a handle and a trigger that a user manually utilizes to move and direct an oscillating sagittal cutting blade 10 in the longitudinal/axial cut direction 15 along a cutting pathway to and through bone or other tissue. The user (e.g., a surgeon) must thereby manually provide inputs to the robot by physically moving it.

It is noted that some such haptic robotic cutting systems may define a cutting area/zone and a non-cutting area/zone, and actively prevent a user form translating the oscillating sagittal cutting blade 10 into/through the non-cutting area to protect areas of a patient that should not be cut (e.g., accidently). However, such robotic systems do not actively or autonomously translate the cutting tool through the cutting area, as the user must physically move the oscillating sagittal cutting blade 10 to an insertion point and through the bone or other tissue in the longitudinal/axial cut direction 15 along a cut path within the cutting area.

Haptic robotic cutting systems thereby require one or both of a user's hands to manually physically guide the cutting tool (and drive mechanism) to and through cut paths (extending in the longitudinal/axial cut direction 15). As surgeons and surgical technicians often do not have both of their hands readily available during surgical procedures, haptic robotic cutting systems are problematic. As haptic robotic cutting systems require user initiated cutting, they systems are relatively demanding on users (e.g., surgeons), limits a user's ability to perform other tasks (the suer loses use of at least one hand), and the robotic system often physically interfered with access to the patient. Still further, as current haptic robotic cutting systems require a user to physically define or control the cut paths of sagittal cutting blades 10, the location, quality, timing and pattern of cuts made with the sagittal cutting blade 10 are reliant on the skill of the user.

Active surgical robotic systems and related active surgical robotic methods that utilize sagittal cutting blades 10 and fully autonomously follow predetermined cut paths extending in the longitudinal/axial cut direction 15, without a user physically engaging and guiding the sagittal cutting blades 10, are thereby desirable. Such active surgical robotic systems that can perform the TKA resections with a sagittal cutting blade 10, while safely and reliably avoid critical anatomy, would be highly desirable. Fully autonomous or active TKA resection robotic systems and related methods that autonomously follow determined cut paths (e.g., of a sagittal cutting blade 10) would be advantageous to allow the user (e.g., surgeon) to perform other tasks.

To facilitate fully autonomous or active TKA resection robotic systems and related methods that autonomously follow determined cut paths of a sagittal cutting blade 10, the present disclosure provides optimized cut paths that extend in the longitudinal/axial cut direction 15 for active robotic execution via a sagittal cutting blade 10. The disclosed robotic TKA sagittal cutting blade 10 cut paths overcome the limitations of sagittal cutting blades 10 (e.g., the longitudinal/axial cut direction 15) and clinical constraints of TKA for an active robot using a sagittal cutting blade 10. The optimized cut paths for sagittal cutting blades and robotic systems of the present disclosure facilitates execution of the TKA resection cuts with a sagittal cutting blade 10 via an active/autonomous surgical robotic system. Thereby, the optimized cut paths provide for TKA resections with active (i.e., fully autonomous) surgical robotic systems that allow a user to use both of their hands for other tasks and free up working space about the robotic system, while ensuring safe, accurate, proper and efficient cuts/resections.

While certain aspects of conventional technologies have been discussed to facilitate disclosure of Applicant's inventions, the Applicant in no way disclaims these technical aspects, and it is contemplated that the inventions may encompass one or more conventional technical aspects.

In this disclosure, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

The present inventions may address one or more of the problems and deficiencies of current robotic systems and TKA resection systems and methods. However, it is contemplated that the inventions may prove useful in addressing other problems and deficiencies in a number of technical areas. Therefore, the claimed invention(s) should not necessarily be construed as limited to addressing any of the particular problems or deficiencies discussed herein.

The present disclosure is generally directed to surgical robots, surgical robotic systems and related surgical methods that include a controller that allows a user to electronically control parameters of movement of a cutting tool along a prescribed or determined cut path. The present disclosure provides configurations and methods of facilitating user inputs to an active or autonomous robotic system to control parameters of movement of a cutting tool along a prescribed or determined cut path. The surgical robotic systems and related surgical methods provide an electronic controller that provides intuitive user control of an active robot along a prescribed or determined cut path thereof.

In some embodiments, the present disclosure provides for fully autonomous or active TKA resection robotic systems and related methods that autonomously follow determined/programmed optimized cut paths with a sagittal cutting blade 10. The cut paths are optimized with respect to the limitation of sagittal cutting blades 10 (e.g., the longitudinal/axial cut direction 15), and the clinical limitations and considerations associated with the resections in a TKA procedure (e.g., avoidance of critical structures that cannot be cut, creating limited entry windows and cut pathways).

The optimized cut paths for sagittal cutting blades and robotic systems of the present disclosure thereby facilitate execution of the TKA resection cuts with a sagittal cutting blade 10 via an active/autonomous surgical robotic system. The optimized cut paths provide for TKA resections (and other similar orthopedic procedures or resections) with active surgical robotic systems, which allow a user to use both of their hands for other tasks, free up working space about the robotic system, perform the resections with increased speed as compare to haptic robotic systems and/or resection using rotary cutting tools, execute challenging cuts with more accuracy than haptic robotic systems, and generally place less demands on a user than with haptic robotic systems. The active/autonomous TKA resection surgical robotic systems and methods of the present disclosure are configured to spatially translate the sagittal cutting blade 10 through a series of ordered coordinates (i.e., a cutting pathway) that are optimized for the sagittal cutting blade 10 and the anatomy associated with each particular TKA resection. For example, the active/autonomous TKA resection surgical robotic systems and methods utilize optimized cutting pathways which unexpectedly allow for a sagittal cutting blade 10 and yet avoid critical anatomy.

In one aspect, the present disclosure provides an active robotic system comprising: an articulated arm comprising a plurality of arm segments defining longitudinal axes, and adjustable joints coupled between adjacent arm segments that are configured to adjust the orientation of the axes of the adjacent arm segments; a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway. The robotic system is configured to autonomously adjust the relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon.

In some embodiments, the plurality of optimized programmed cut paths comprise a first series of cut paths that are configured to create a tibial resection on the proximal tibia while preventing injury to the patient's patellar tendon, medial collateral ligament (MCL), lateral collateral ligament (LCL), and posterior cruciate ligament (PCL). In some such embodiments, the first series of cut paths are configured to enter the joint space between the patient's proximal tibia and the distal femur via an entry region on an anterior-medial bone region, and the trajectories of the cut paths of the first series of cut paths extend between the patient's MCL and patellar tendon. In some such embodiments, the first series of cut paths comprise a first counterclockwise anterior to posterior trajectory cut path that arcuately extends along a lateral bone boundary of the proximal tibia, and a second anterior to posterior clockwise trajectory cut path that arcuately extends along a medial bone boundary of the proximal tibia. In some such embodiments, the first series of cut paths further comprise at least one third cut path that extends between the first and second cut paths of the first serios of cut paths to remove portions of the proximal tibia that extend between the first and second cut paths to form the tibial resection.

In some embodiments, the plurality of optimized programmed cut paths comprise a second series of cut paths that are configured to create distal femur resections on medial and lateral condyles of the distal femur while preventing injury to the patient's quadriceps tendon, MCL, popliteal tendon, and LCL. In some such embodiments, the second series of cut paths are configured to enter the joint space between the patient's proximal tibia and the distal femur via an entry region on the anterior side of the posterior femur, and the trajectories of the cut paths of the second series of cut paths extend therethrough in an anterior to posterior direction. In some such embodiments, the second series of cut paths comprises a first subseries of cut paths extending through a portion of the medial condyle of the distal femur, and wherein the first subseries of cut paths comprises a first counterclockwise anterior to posterior trajectory cut path through a medial side of the medial condyle that arcuately extends along a medial bone boundary of the distal femur, and a second clockwise anterior to posterior trajectory cut path through a lateral side of the medial condyle that arcuately extends along a lateral bone boundary of the distal femur. In some such embodiments, the first subseries of cut paths further comprises at least one third cut path trajectory that extends anterior to posterior and between the first and second cut paths of the first subseries of cut paths to remove portions of the distal femur that extend between the first and second cut paths to form distal femur resection on medial condyle. In some such embodiments, the second series of cut paths comprises a second subseries of cut paths extending through a portion of the lateral condyle of the distal femur, and wherein the second subseries of cut paths comprises a third counterclockwise anterior to posterior trajectory cut path through a medial side of the lateral condyle of the distal femur that arcuately extends along a medial bone boundary of the distal femur, and a fourth generally clockwise anterior to posterior trajectory cut path through a lateral side of the lateral condyle of the distal femur that extends along a lateral bone boundary of the distal femur.

In some embodiments, the plurality of optimized programmed cut paths comprise a third series of cut paths that are configured to create posterior femur resections on medial and lateral condyles of the posterior femur while preventing injury to the patient's quadriceps tendon, MCL, popliteal tendon, and LCL. In some such embodiments, the third series of cut paths are configured to enter the joint space between the patient's proximal tibia and the distal femur via an entry region on the distal side of the posterior femur, and the trajectories of the cut paths of the third series of cut paths extend therethrough in a distal to proximal direction. In some such embodiments, the third series of cut paths comprises a third subseries of cut paths extending through a portion of the medial condyle of the posterior femur, and wherein the third subseries of cut paths comprises a first clockwise distal to proximal substantially linear trajectory cut path through a medial side of the medial condyle that extends substantially linearly along a medial bone boundary of the posterior femur, and a second counterclockwise distal to proximal substantially linear trajectory cut path through a lateral side of the medial condyle that extends substantially linearly along a lateral bone boundary of the posterior femur. In some such embodiments, the third series of cut paths comprises a fourth subseries of cut paths extending through a portion of the lateral condyle of the posterior femur, and wherein the fourth subseries of cut paths comprises a third clockwise proximal to distal trajectory cut path through a medial side of the lateral condyle of the posterior femur that extends substantially linearly along a medial bone boundary of the posterior femur, and a fourth generally counterclockwise distal to proximal substantially linear trajectory cut path through a lateral side of the lateral condyle of the posterior femur that extends substantially linearly along a lateral bone boundary of the posterior femur.

In some embodiments, the plurality of optimized programmed cut paths comprise a fourth series of cut paths that are configured to create posterior chamfer resection on medial and lateral condyles of the femur that extend between the posterior-distal femur while preventing injury to the patient's quadriceps tendon, MCL, and LCL. In some such embodiments, the fourth series of cut paths are configured to enter the joint space between the patient's proximal tibia and the distal femur via an entry region on the distal side of the posterior-distal femur, and the trajectories of the cut paths of the fourth series of cut paths extend therethrough in a distal to proximal direction. In some such embodiments, the fourth series of cut paths comprises a fifth subseries of cut paths extending through a portion of the medial condyle of the posterior-distal femur, and wherein the fifth subseries of cut paths comprises a first clockwise distal to proximal substantially linear trajectory cut path through a medial side of the medial condyle that extends substantially linearly along a medial bone boundary of the posterior-distal femur, and a second counterclockwise distal to proximal substantially linear trajectory cut path through a lateral side of the medial condyle that extends substantially linearly along a lateral bone boundary of the posterior-distal femur. In some such embodiments, the fourth series of cut paths comprises a sixth subseries of cut paths extending through a portion of the lateral condyle of the posterior-distal femur, and wherein the fourth subseries of cut paths comprises a third clockwise proximal to distal trajectory cut path through a medial side of the lateral condyle of the posterior-distal femur that extends substantially linearly along a medial bone boundary of the posterior-distal femur, and a fourth generally counterclockwise distal to proximal substantially linear trajectory cut path through a lateral side of the lateral condyle of the posterior-distal femur that extends substantially linearly along a lateral bone boundary of the posterior-distal femur.

In some embodiments, the plurality of optimized programmed cut paths comprise a fifth series of cut paths that are configured to create anterior chamfer resection on medial and lateral condyles of the femur that extend between the anterior-distal femur while preventing injury to the patient's quadriceps tendon, MCL, and LCL. In some such embodiments, the fifth series of cut paths are configured to enter the joint space between the patient's proximal tibia and the distal femur via an entry region on the distal side of the anterior-distal femur, and the trajectories of the cut paths of the fifth series of cut paths extend therethrough in a distal to proximal direction. In some such embodiments, the fifth series of cut paths comprises a seventh subseries of cut paths extending through a portion of the medial condyle of the anterior-distal femur, and wherein the seventh subseries of cut paths comprises a first distal to proximal substantially linear trajectory cut path through the medial condyle. In some such embodiments, the fifth series of cut paths comprises an eighth subseries of cut paths extending through a portion of the lateral condyle of the anterior-distal femur, and wherein the eighth subseries of cut paths comprises a second distal to proximal substantially linear trajectory cut path through the lateral condyle.

In some embodiments, the plurality of optimized programmed cut paths comprise a sixth series of cut paths that are configured to create anterior femur resections on medial and lateral condyles of the anterior femur while preventing injury to the patient's quadriceps tendon, MCL, popliteal tendon and LCL. In some such embodiments, the sixth series of cut paths are configured to enter the joint space between the patient's proximal tibia and the distal femur via an entry region on the distal side of the anterior femur, and the trajectories of the cut paths of the sixth series of cut paths extend therethrough in a distal to proximal direction. In some such embodiments, the sixth series of cut paths comprises a ninth subseries of cut paths extending through a portion of the medial condyle of the anterior femur, and wherein the ninth subseries of cut paths comprises a first substantially linear distal to proximal trajectory cut path through the medial condyle. In some such embodiments, the sixth series of cut paths comprises a tenth subseries of cut paths extending through a portion of the lateral condyle of the anterior femur, and wherein the tenth subseries of cut paths comprises a second clockwise substantially linear distal to proximal trajectory cut path through the medial side of the lateral condyle extending substantially linearly along a medial bone boundary of the anterior femur, and a third counterclockwise proximal to distal trajectory cut path through the lateral side of the lateral condyle extending arcuately along a lateral bone boundary of the anterior femur.

In some embodiments, the plurality of optimized programmed cut paths are programmed in memory of the robotic system. In some such embodiments, the robotic system is configured to autonomously execute the plurality of optimized programmed cut paths via the sagittal cutting blade without a user physically guiding the sagittal cutting blade.

In another aspect, the present disclosure provides a method of resecting of portions of a proximal tibia and/or a distal femur of a patient to facilitate implantation of a femoral component and a tibial component, respectively, of a total knee arthroplasty prosthesis thereon, comprising utilizing any of the robotic systems disclose above to autonomously execute at least some of the plurality of optimized programmed cut paths to autonomously resect at least one portion of the proximal tibia and/or the distal femur.

It should be appreciated that all combinations of the foregoing aspects and additional concepts discussed in greater detail below (provided such concepts are not mutually inconsistent) are contemplated as being part of the inventive subject matter and to achieve the advantages disclosed herein.

These and other objects, features and advantages of this disclosure will become apparent from the following detailed description of the various aspects of the disclosure taken in conjunction with the accompanying drawings.

BRIEF DESCRIPTION OF THE DRAWINGS

These and other features, aspects, and advantages of the present disclosure will become better understood when the following detailed description is read with reference to the accompanying drawings, which are not necessarily drawn to scale and in which like reference numerals represent like aspects throughout the drawings, wherein.

DETAILED DESCRIPTION

Figure 1:
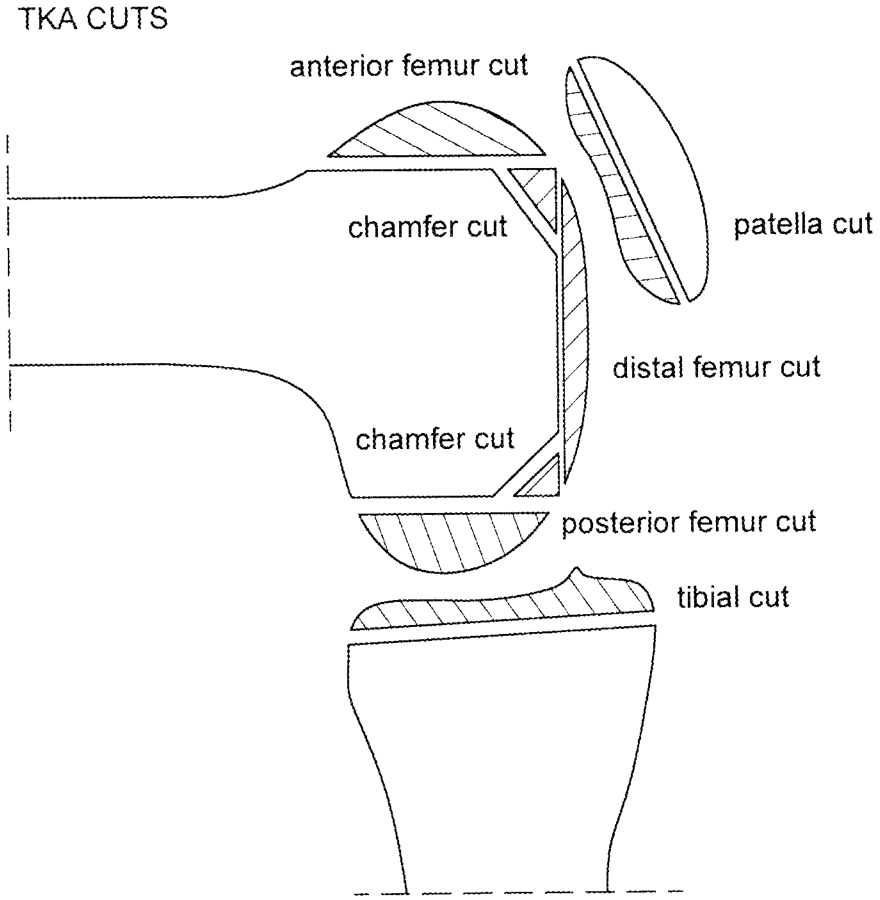
FIG. 1 Prior Art
FIG. 1 illustrates, in one example, total knee arthroplasty (TKA) resections of a proximal tibia and a distal femur, in accordance with one or more aspects of the present disclosure.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to +5%, such as less than or equal to +2%, such as less than or equal to #1%, such as less than or equal to +0.5%, such as less than or equal to +0.2%, such as less than or equal to +0.1%, such as less than or equal to +0.05%. In some instances, the approximating language may correspond to the precision of an instrument for measuring the value. Any examples of operating or configuration parameters are not exclusive of other parameters of the disclosed embodiments.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

The term "coupled" and like terms are used herein to refer to both direct and indirect connections. As used herein and unless otherwise indicated, the term "entirety" (and any other form of "entire") means at least a substantial portion, such as at least 95% or at least 99%. The term "entirety" (and any other form of "entire"), as used herein, is thereby not limited to 100%, unless otherwise indicated. As used herein, the term "layer"

The term "boundary," "edge," "periphery" and the like terms and phrases when used herein in reference to a bone or bone portion (e.g., extends along a bone boundary) are to be understood (and utilized herein as such) to refer to a portion of a bone that is positioned immediately adjacent to or proximate to an outer edge, limit or margin of the bone or bone portion. It is noted that such bone portion may include a respective outer bone edge, limit or margin, or be spaced slightly away from but substantially near the respective bone outer edge, limit or margin, such as being within 6 mm, 5 mm, 4 mm, 3 mm, 2 mm or 1 mm of the respective bone outer edge, limit or margin.

Components, aspects, features, configurations, arrangements, uses and the like described, illustrated or otherwise disclosed herein with respect to any particular embodiment may similarly be applied to any other embodiment disclosed herein.

Figure 3:
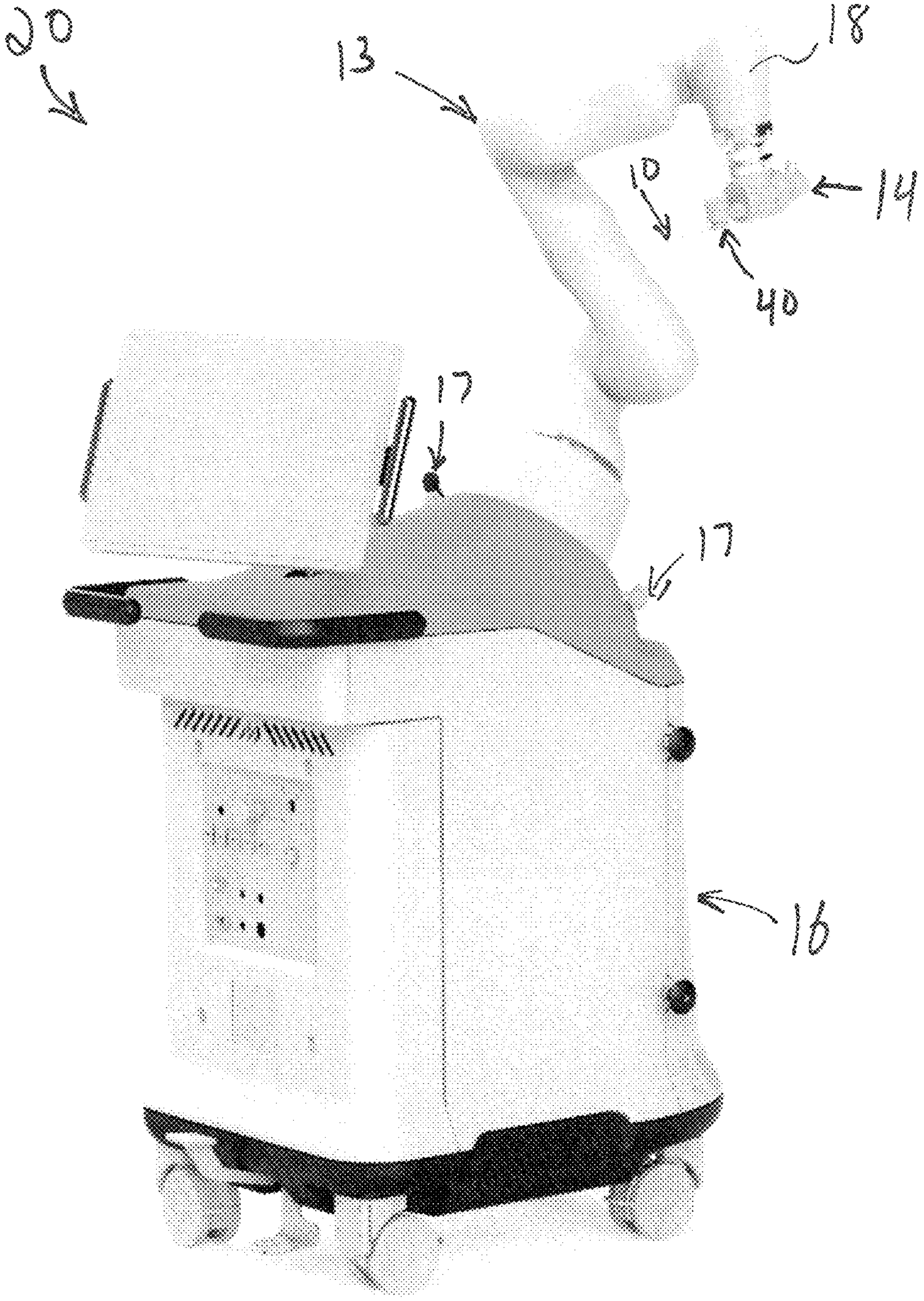
FIG. 3 illustrates, in one example, a perspective view of a TKA resection active robotic system utilizing the sagittal cutting blade of FIG. 3, in accordance with one or more aspects of the present disclosure.
Figure 4:
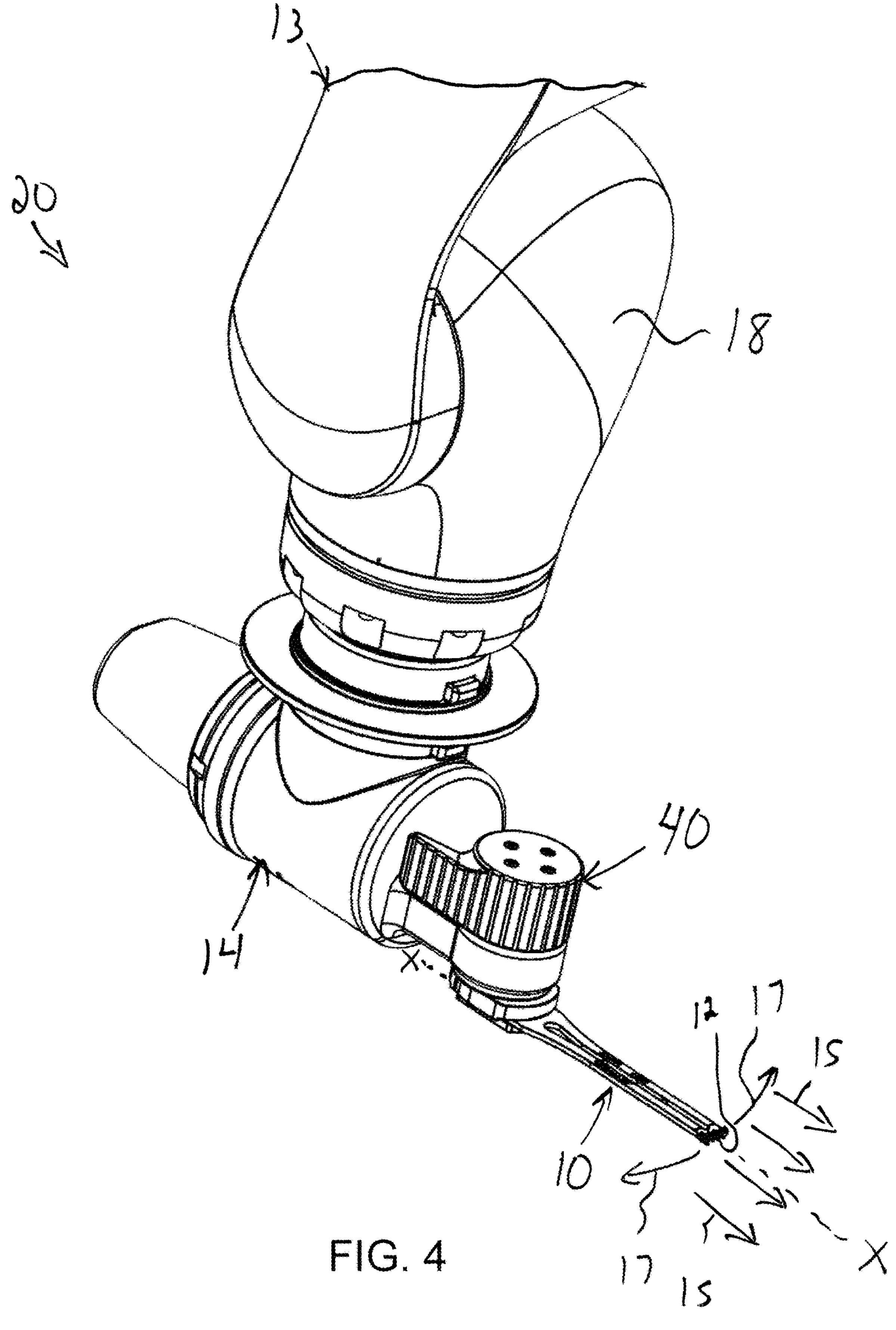
FIG. 4 illustrates, in one example, an elevational perspective view of an arm segment, end effector and the sagittal cutting blade of the active robotic system of FIG. 3, in accordance with one or more aspects of the present disclosure.

As shown in FIGS. 3 and 4, a robot or robotic system 20 according to the present disclosure may include, inter alia, an articulated robotic arm 13, an end effector 14 and a sagittal cutting blade 10. As depicted in FIGS. 3 and 4, the robotic system 20 may be configured as a surgical robot. For example, the surgical robot 20 may be biocompatible, and configured be sterilized to such a degree, as required in surgical settings. However, in other embodiments, the robot 20 may be configured as an industrial or other non-surgical robotic devices or systems.

The term "surgical robot" as used herein in reference to the exemplary illustrative robot/robotic system embodiments, and is not meant in a limiting sense, and any and all description herein directed to a "surgical robot" or the like equally applies to a generic robot/robotic system or an industrial or other non-surgical robot/robotic system. It is noted, however, that the sagittal cutting paths provide herein have particular application with surgical active/autonomous robotic systems 10 for TKA resections.

Figure 11:
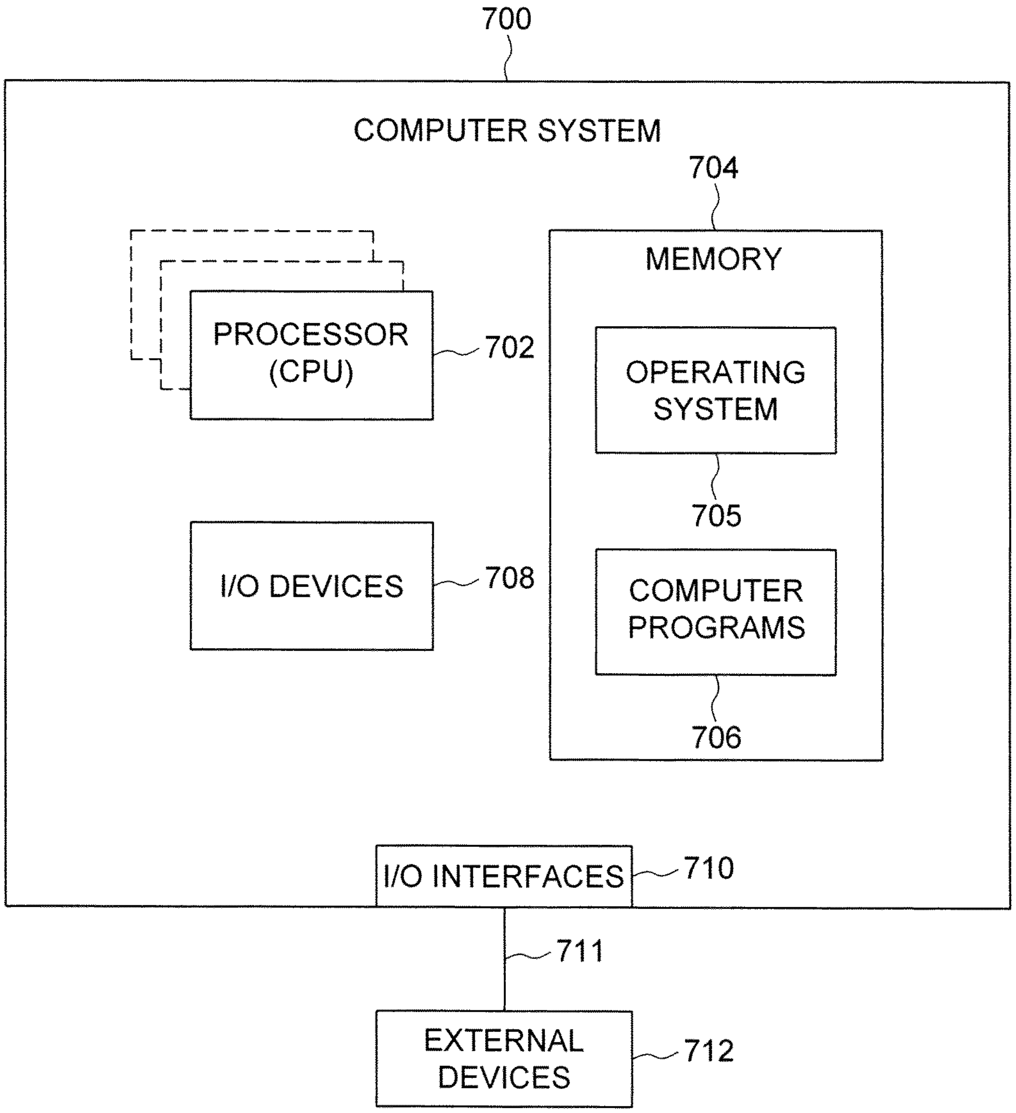
FIG. 11 illustrates, in one example, a graphic representation of a computer system and associated devices to incorporate and/or use aspects described herein, in accordance with one or more aspects of the present disclosure.

The robotic system 20 may be operably connected to a computer system (e.g., memory, processor, etc.), as shown in FIG. 11 for example, that controls movement of the sagittal cutting blade 10 along one or more determined, prescribed or programmed cut paths, via movement of the articulated arm 13 for example, and potentially operation of the end effector 14. For example, in some embodiments, the robotic system 20 may comprise a control unit with programming, and potentially a user interface (UI). The control unit may include at least one processing circuit, at least one input/output device, and at least one storage device or memory having at least one database or cutting instructions stored therein. The control unit may have a control algorithm or programming code for controlling the position of the sagittal cutting blade 10 (such as via the joint angle between segments of the articulated arm 13, for example). The control algorithm or programming code may be a default control algorithm or include inputs from, for example, the UI and/or another interface.

As shown in FIGS. 3 and 4, the articulated arm 13 may extend from a base and include a plurality of rigid arm or body segments/parts, and a plurality of joints that connect adjacent segments (and a first or base segment to the base). The plurality of joints may include, for example, four, five or six individual segments that are coupled together via three, four or five joints, respectively. In some other embodiments, the articulated arm 13 may include at least two segments and at least one joint coupling the at least two segments together, or more than six segments and more than five joints coupling the segments together.

Each arm segment of the articulated arm 13 may define an axial axis extending along its longitudinal length. The joints may be configured such that the arm segments can rotate about their axes and/or articulate angularly with respect to each other such that the axes of adjacent segments are angularly offset. In some embodiments, one or more of the joints may be configured to allow multiple degrees of freedom between adjacent arm segments (and, potentially, the base segment and the base). In some such embodiments, at least one of the joints may be configured to provide six degrees of freedom.

The articulated arm 13 may further comprise motors, actuators or other adjustment devices that are configured to adjust the axial rotation and/or angular orientation between adjacent segments. In this way, the robotic system 20 can control the arrangement of the articulated arm 13 to translate the sagittal cutting blade 10 three-dimensionally in space and relative to a workpiece (e.g., a patient, such as a tibia and femur thereof) to, ultimately, cut one or more portions of the workpiece (e.g., proximal tibia and the distal femur). As noted above, the robotic system 20 may include control software that dictates or instructs, inter alai, the articulated arm 13 of the robotic system 20 to adjust in particular ways (i.e., adjustment of the joints) to accomplish determined, prescribed or programmed cut path movements of the sagittal cutting blade 10 that are optimized for TKA resections with the sagittal cutting blade 10. Stated differently, the robotic system 20 may include control software that dictates or instructs, inter alai, the articulated arm 13 of the robotic system 20 to adjust in particular ways (i.e., adjustment of the joints) to translate the sagittal cutting blade 10 in three-dimensional space along one or more (e.g., a series or a plurality of) optimized determined, prescribed or programmed cut paths of the sagittal cutting blade 10 to make resections along or according to the determined, prescribed or programmed cut paths.

The optimized cut paths are described further below in detail. The paths of the sagittal cutting blade 10 may thereby be predetermined, pre-prescribed or pre-programmed in the robotic system 20 such that the user does not dictate the cut paths of the sagittal cutting blade 10 that the sagittal cutting blade 10 travels along to make the TKA resections.

The base of the surgical robotic system 20 may be fixed to, for example, a movable cart 16 as shown in FIG. 3, or the ground, such that the base may provide a fixed frame of reference for defining the position, orientation, and motion of the plurality of joints and the plurality of arm segments relative to the base. The base may be used to define a frame of reference, such as, for example, a set of three-dimensional axes (e.g., x, y, z), which may be used to define positions, orientations, and motions of the surgical robotic system 20 and of objects relative to the surgical robotic system 20. In some embodiments, the movable cart 16 may include one or more fiducials 17 (e.g., a fiducial array) so that a camera system can be utilized to determine the location of the base of the arm 13 (or the robot 20 generally) as a frame of reference, as shown in FIG. 3. A frame of reference defined relative to the base 19 may also be known as a world frame, a base, a base frame, a frame, or a tool frame. It is noted that with the position and orientation of an object defined or calculated in relation to the fixed frame of reference, the object may also be defined in the same frame of reference as the robotic system 20, and the surgical robotic system 20 may calculate the position and orientation of the object. As such, the surgical robotic system 20 may programmably interact with the defined objects, positions, and/or orientations. In some embodiments, the system 20 may be configured to recognize (e.g., detect and/or identify) anatomical structures that are proximate to the bone portions to be cut (e.g., other bones, such as adjacent bones) and prevent the system 20 from cutting such anatomical structures. Accordingly, the system 20 may have a collision avoidance feature that prevents the system 20 from cutting anatomical structures other than specified bone portions, for example.

As shown in FIGS. 3 and 4, the robotic system 20 may include an end effector 14 coupled (e.g., rotatably coupled) to an end, last or termination arm segment 18 of the articulated arm 13, such as via a rotatable connector assembly therebetween. The rotatable connector assembly may be configured such that the end effector 14 is rotatable about a longitudinal axis of the end arm segment 18. As shown in FIG. 4, the end effector 14 may be configured such that the axis of the end arm segment 18 and the axis X-X of the sagittal cutting blade 10, along which the cutting direction 15 of the sagittal cutting blade 10 extends, are angled with respect to each other. In the illustrated exemplary embodiment, the axis X-X of the sagittal cutting blade 10 (and the cutting direction 15 that the sagittal cutting blade 10 is configured to cut) and the axis of the end arm segment 18 are oriented perpendicular (or normal) to each other. Likewise, the end effector may define a longitudinal axis that is substantially parallel to the axis X-X of the sagittal cutting blade 10 (and the cutting direction 15 that the sagittal cutting blade 10 is configured to cut), and/or angled (e.g., perpendicular) to the axis of the end arm segment 18, as shown in FIGS. 3 and 4.

Referring further to FIGS. 3 and 4, since the position, orientation, and motion of the plurality of joints and the plurality of arm segments relative to the base may be defined, and the angular orientation of the end effector 14 with respect to the end arm segment 18 of the articulated arm 13, the position and orientation of the sagittal cutting blade 10 extending from the end effector 14 can be calculated or determined by the robotic system 20. It is understood that the exemplary illustrative sagittal cutting blade 10 is configured for cutting bone or other tissue. In some other embodiments, the sagittal cutting blade 10 may be replaceable with a different cutting tool or a non-cutting implements that may function as, for example, a marking device or a viewing device.

As described above and shown in FIGS. 2 and 4, the sagittal cutting blade 10 of the exemplary robotic system 20 may include an attachment, tang or hub portion at a proximal end portion that couples with an attachment mechanism 40 of the end effector 14. For example, the end effector 14 may include a chuck or other attachment mechanism 40 configured to mate with the attachment portion of the sagittal cutting blade 10, and removably secure the sagittal cutting blade 10 and the end effector 14 together. The end effector 14 may thereby be capable of physically translating or moving the sagittal cutting blade 10 along the cutting pathway 17 along which the sagittal cutting blade 10 is configured to cut. The axis X-X of the sagittal cutting blade 10 may extend through the attachment portion 40 and the end effector 14, and the sagittal cutting blade 10 (and the end effector 14) may be longitudinally extended along the axis X-X. The end effector 14 may be configured to provide a rotation or torque to the sagittal cutting blade 10 such that it is rotated along the cutting pathway 17 about an oscillation axis, for example.

As described above and shown in FIGS. 2-4, the sagittal cutting blade 10 may comprise a saw blade with a thin, flat, elongated shape, with a cutting edge 12 at a distal tip or end portion of a blade body portion. The thin, flat design may minimize the size of the blade's kerf and allow the blade 10 to make an accurate, straight cut. The cutting edge 12 may be generally oriented along a direction that is orthogonal to the direction of blade elongation and contains a plurality of teeth and/or abrasives. Thus, when the sagittal cutting blade 10 is translated/oscillated along the cutting pathway 17, the cutting edge 12 can be translated in the axial/longitudinal cutting direction 17 along a cut path such that the cutting edge 12 engages and cuts into and through a portion of a bone (e.g., proximal tibia and the distal femur) as it is translated along the cutting path.

Figure 2:
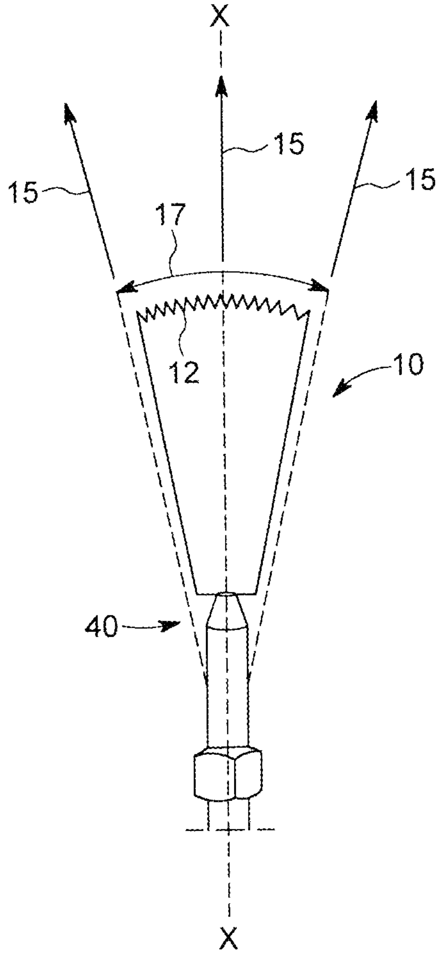
FIG. 2 Prior Art
FIG. 2 illustrates, in one example, a top view of a sagittal cutting blade coupled with an attachment mechanism, in accordance with one or more aspects of the present disclosure.

With reference to FIGS. 2 and 4, in some embodiments, the end effector 14 may thus be configured to oscillate (i.e., translate in a back and forth manner) the sagittal cutting blade 10 in a or along the oscillatory cutting direction or pathway 17. As explained above, the oscillatory cutting pathway 17 may extend along a plane defined by the blade 10. The sagittal cutting blade 10 performs a cutting action by being translated in the cut direction 17 extending along the longitudinal axis X-X (e.g., via the articulated arm 13, at least in part) (i.e., longitudinally/axially) in a direction extending from the coupling portion to the tip portion thereof as the blade 10 (and the cutting edge 12 thereof) is being oscillated along the oscillatory cutting pathway 17 (i.e., in cutting strokes). Because of the motion along the oscillatory cutting pathway 17 applied by the end effector 14, and the forward axial/longitudinal pressure applied by the robotic system 20 (e.g., via the articulated arm 13, at least in part) along the cut path, the teeth of the cutting edge 12 of the sagittal cutting blade 10 can cut and separate bone tissue.

As explained further below with respect to FIGS. 5A-10B, the robotic system 20 may include a plurality of optimized determined, prescribed or programmed cut paths of the sagittal cutting blade 10 to effectuate resection of bone, such as the TKA resections of the proximal tibia and the distal femur. The optimized cut paths may be controlled or effectuated by control software that dictates or instructs, inter alai, the articulated arm 13 of the robotic system 20 to adjust in particular ways (i.e., adjustment of the joints) to translate the sagittal cutting blade 10 in three-dimensional space along the optimized determined, prescribed or programmed cut paths of the sagittal cutting blade 10 to cut a bone along or according to the determined, prescribed or programmed cut paths. It is noted that the end effector 14 translates/oscillates the sagittal cutting blade 10 along the cutting pathway 17 while the robotic system 20 is translating the sagittal cutting blade 10 (via the articulated arm 13, at least partially) along the determined, prescribed or programmed cut paths in the longitudinal/axial cutting direction 15.

The cut paths of the sagittal cutting blade 10 are thereby predetermined, pre-prescribed or pre-programmed in the robotic system 20 such that the user does not dictate the cut paths of the sagittal cutting blade 10 along which the sagittal cutting blade 10 travels to make the TKA bone resections, for example. It is noted that the cut paths may thereby include entry positions where the sagittal cutting blade 10 first initiates cutting of a portion of the proximal tibia and the distal femur and enters the bone portion, as well as three-dimensional spatial pathways extending from the entry positions through the bone portion. In some embodiments, the systems and methods discussed herein may include cutting blade 10 paths such that the cutting blade 10 is oriented/positioned furthest medially and/or is angled furthest medially at the entry positions as the anatomical structures proximate to the bone/bone portions to be but would allow for (i.e., that would not damage the anatomical structures proximate to the bone/bone portions to be cut).

As shown in FIGS. 5A-10B, in some embodiments, the cut paths comprise spatial pathways to and through bone portions, such as portions of the proximal tibia and the distal femur to make the necessary TKA resections thereof (as shown in FIG. 1). The cut paths may thereby be configured to resect or cut bone according to requirements of a surgical procedure, such as to resect portions of the proximal tibia and the distal femur for TKA. For example, the cut paths may be configured to resect portions of the proximal tibia and the distal femur for the cooperation of TKA proximal tibia and the distal femur implants therewith.

The optimized cut paths of the active/autonomous surgical robotic systems for TKA resection via a sagittal cutting blade 12 will now be discussed. It is noted that numerical terms such as "first," "second," "third" and the like are utilized only for references purposes of the cut paths to distinguish the cut paths from each other, and does not specific the particular order that the cut paths are made by the sagittal cutting blade 10/active robotic system 20.

It is also noted that the cut paths described herein represent the general or overall spatial pathway of the cutting edge 12 of the sagittal cutting blade 10 as it is translated via the active/autonomous robotic system 10 to and through the respective bone portion (i.e., during a cutting operation). A cut path may be formed or completed via a single continuous cutting motion or advancement of the cutting tool/blade 10 directly along the respective pathway. A cut path may also be formed or completed via a plurality of consecutive separate and distinct cutting motions or advancements of the cutting tool/blade 10 that cooperatively extend along the respective pathway. For example, the system 20 can be programmed to perform a series of small advancements or intermediate cutting paths (which may or may not be sequential) that each remove small amounts of bone along a given vector (i.e., peck at the bone). The cutting tool/blade 10 may stop, move backwards or otherwise translate off of the cut path between the small advancements or intermediate cutting paths, but the collective bone removal of the series of small advancements or intermediate cutting paths may form the respective cut path. A cut path, as used herein, is thus the overall pathway or trajectory of removed bone portions during a cutting operation. The actual movement of the cutting tool/blade 10 that forms the cut path may or may not extend directly along the cut path. Accordingly, a cut path disclosed herein does not require that the cutting blade 10 move continuously along a given path or trajectory, but rather represents a generalized direction of bone removal without reference to exactly how the cutting blade 10 exactly cut/remove the bone tissue, but rather is the end result of an overall cutting operation. It is also notes that cut paths may or may not overlap with each other.

Figure 5B:
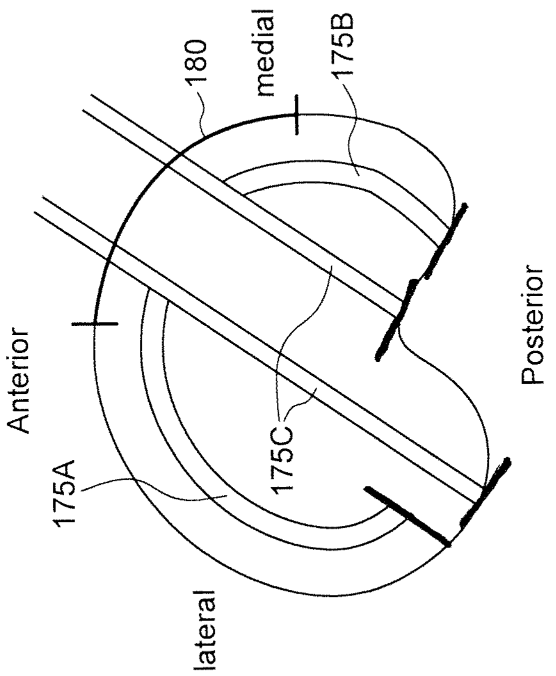
FIGS. 5A and 5B illustrate an exemplary first series of programmed sagittal cut paths of the active robotic system of FIG. 3 for forming the TKA resection of FIG. 1, in accordance with one or more aspects of the present disclosure.
Figure 5A:
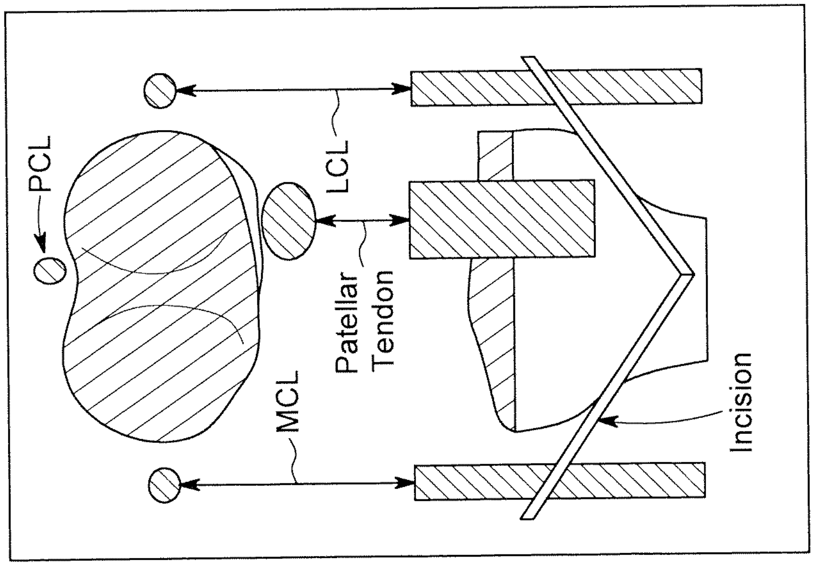

With reference to FIGS. 1, 5A and 5B, the optimized determined, prescribed or programmed (i.e., predetermined, pre-prescribed or preprogrammed) cut paths of the sagittal cutting blade 10 of the active/autonomous TKA surgical robotic system 10 and related methods of the present disclosure comprise optimized programmed cut paths 175 configured to create a tibial resection on the proximal tibia, as described above. As shown in FIGS. 1 and 5A, the programmed cut paths 175 for creating the tibial resection (on the proximal tibia) are configured to avoid cutting or otherwise injuring/damaging the patient's patellar tendon, medial collateral ligament (MCL), lateral collateral ligament (LCL), and posterior cruciate ligament (PCL). As shown in FIGS. 5A and 5B, the cut paths 175 are configured to enter the joint space and engage the proximal tibia via an entry region 180 on the anterior-medial bone region, and the trajectories of the cut paths 175 extends therethrough between the patient's MCL and patellar tendon.

As shown in FIG. 5B, the programmed cut paths 175 of the sagittal cutting blade 10 of the active/autonomous TKA surgical robotic system 10 and related method for creating the tibial resection (on the proximal tibia) comprise a first counterclockwise trajectory (anterior to posterior) cut path 175A that arcuately extends along the lateral bone boundary, and a second clockwise trajectory (anterior to posterior) cut path 175B that arcuately extends along the medial bone boundary. As also shown in FIG. 5B, in some embodiments, the programmed cut paths 175 of the sagittal cutting blade 10 for creating the tibial resection may further comprise one or more substantially linear and/or arcuate third cut paths 175C that remove bone that is not cut via the first and second cut paths 175A, 175B. In some embodiments, the sagittal cutting blade 10 may be translated along the one or more third cut paths 175C after being translated along the first and second cut paths 175A, 175B.

Figure 6B:
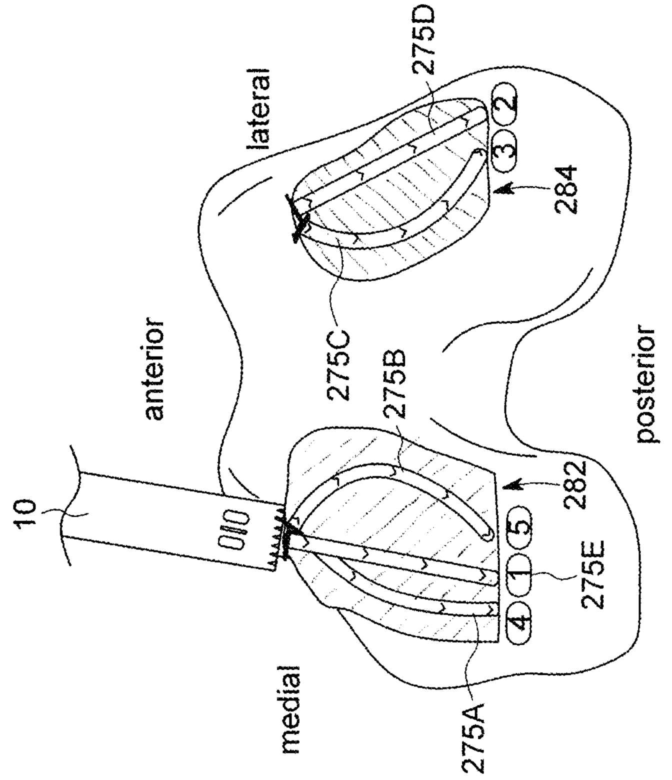
FIGS. 6A and 6B illustrate an exemplary second series of programmed sagittal cut paths of the active robotic system of FIG. 3 for forming the TKA resection of FIG. 1, in accordance with one or more aspects of the present disclosure.
Figure 6A:
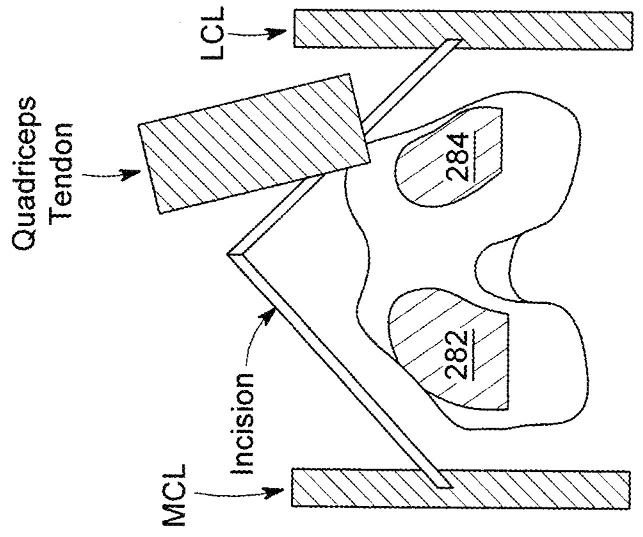

With reference to FIGS. 1, 6A and 6B, the optimized determined, prescribed or programmed cut paths 275 of the sagittal cutting blade 10 of the active/autonomous TKA surgical robotic system 10 and related methods of the present disclosure comprise optimized programmed cut paths 275 configured to create the distal femur resections on the distal femur, as described above. As shown in FIGS. 1 and 6A, the programmed cut paths 275 for creating the distal femur resections (on the distal femur) are configured to avoid cutting or otherwise injuring/damaging the patient's quadriceps tendon, MCL, and LCL. As shown in FIGS. 6A and 6B, the cut paths 275 are configured to enter the joint space and engage the distal femur from the anterior side, and the trajectories of the cut paths 275 extends therethrough anterior to posterior.

As shown in FIG. 6B, the optimized programmed cut paths 275 of the sagittal cutting blade 10 of the active/autonomous TKA surgical robotic system 10 and related method for creating the distal femur resection (on the distal femur) comprise cut paths 275 through portions of the medial condyle 282 and the lateral condyle 284. As shown in FIG. 6B, the optimized programmed cut paths 275 of the sagittal cutting blade 10 through the medial condyle 282 distal femur resection may comprise a first counterclockwise trajectory (anterior to posterior) cut path 275A through the medial side of the medial condyle 282 that arcuately extends along the medial bone boundary, and a second clockwise trajectory (anterior to posterior) cut path 275B through the lateral side of the medial condyle 282 that arcuately extends along the lateral bone boundary. In some embodiments, the optimized programmed cut paths 275 of the sagittal cutting blade 10 through the medial condyle 282 may comprise one or more additional cut paths 275E to remove any bone extending between the first and second cut paths 275A, 275B, as shown in FIG. 6B.

As also shown in FIG. 6B, the optimized programmed cut paths 275 of the sagittal cutting blade 10 through the lateral condyle 284 for distal femur resection may comprise a third counterclockwise trajectory (anterior to posterior) cut path 275C through the medial side of the lateral condyle 284 that arcuately extends along the medial bone boundary, and a fourth generally clockwise trajectory (anterior to posterior) cut path 275D through the lateral side of the lateral condyle 284 that extends linearly (or arcuately) along the lateral bone boundary.

Figure 7A:
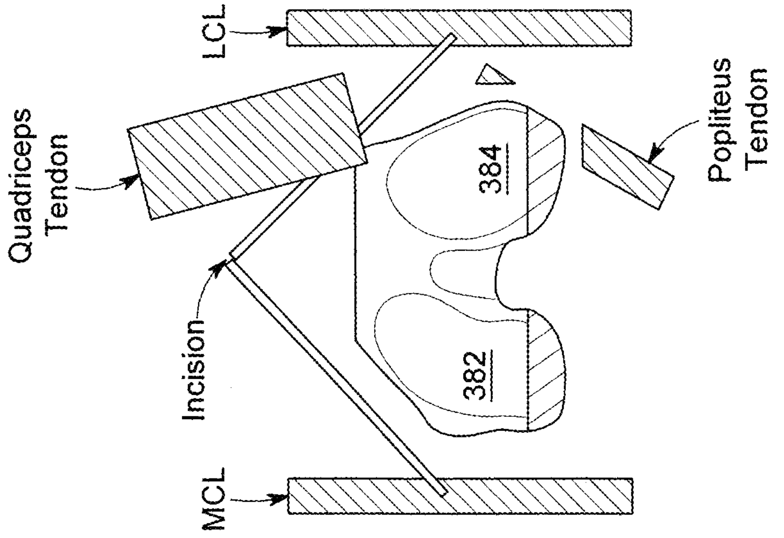
FIGS. 7A and 7B illustrate an exemplary third series of programmed sagittal cut paths of the active robotic system of FIG. 3 for forming the TKA resection of FIG. 1, in accordance with one or more aspects of the present disclosure.
Figure 7B:
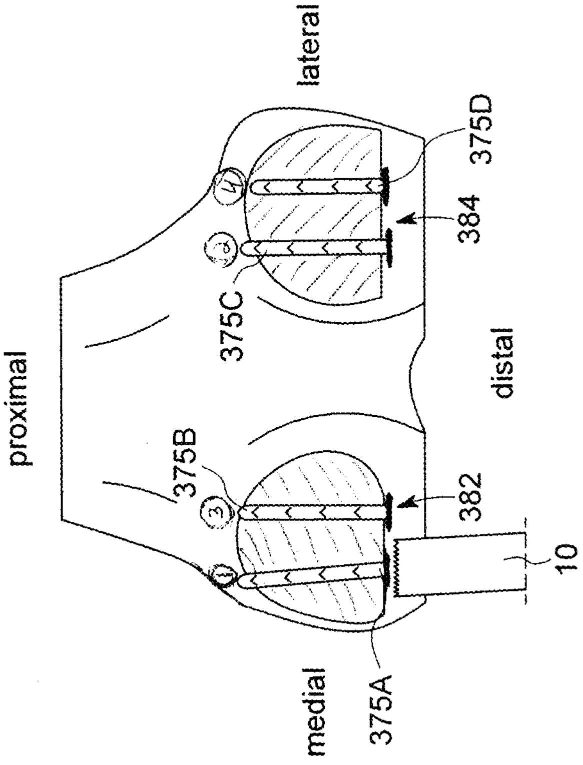

With reference to FIGS. 1, 7A and 7B, the optimized determined, prescribed or programmed cut paths of the sagittal cutting blade 10 of the active/autonomous TKA surgical robotic system 10 and related methods of the present disclosure comprise optimized programmed cut paths 375 configured to create the posterior femur resections on the posterior femur, as described above. As shown in FIGS. 1 and 7A, the programmed cut paths 375 for creating the posterior femur resections (on the posterior femur) are configured to avoid cutting or otherwise injuring/damaging the patient's quadriceps tendon, MCL, popliteal tendon, and LCL. As shown in FIGS. 7A and 7B, the cut paths 375 are configured to enter the joint space and engage the posterior femur from the distal side, and the trajectories of the cut paths 375 extends therethrough distal to proximal.

As shown in FIGS. 7A and 7B, the optimized programmed cut paths 375 of the sagittal cutting blade 10 of the active/autonomous TKA surgical robotic system 10 and related method for creating the posterior femur resections (on the distal femur) comprise cut paths 375 through portions of the medial condyle 382 and the lateral condyle 384. As shown in FIG. 7B, the optimized programmed cut paths 375 of the sagittal cutting blade 10 through the medial condyle 382 for posterior femur resection may comprise a first clockwise linear trajectory (distal to proximal) cut path 375A through the medial side of the medial condyle 382 that extends substantially linearly along the medial bone boundary, and a second counterclockwise linear trajectory (distal to proximal) cut path 375B through the lateral side of the medial condyle 382 that extends substantially linearly along the lateral bone boundary.

As also shown in FIG. 7B, the optimized programmed cut paths 375 of the sagittal cutting blade 10 through the lateral condyle 384 for posterior femur resection may comprise a third clockwise trajectory (proximal to distal) cut path 375C through the medial side of the lateral condyle 384 that extends substantially linearly along the medial bone boundary, and a fourth generally counterclockwise linear trajectory (distal to proximal) cut path 375D through the lateral side of the lateral condyle 384 that extends substantially linearly along the lateral bone boundary.

Figure 8B:
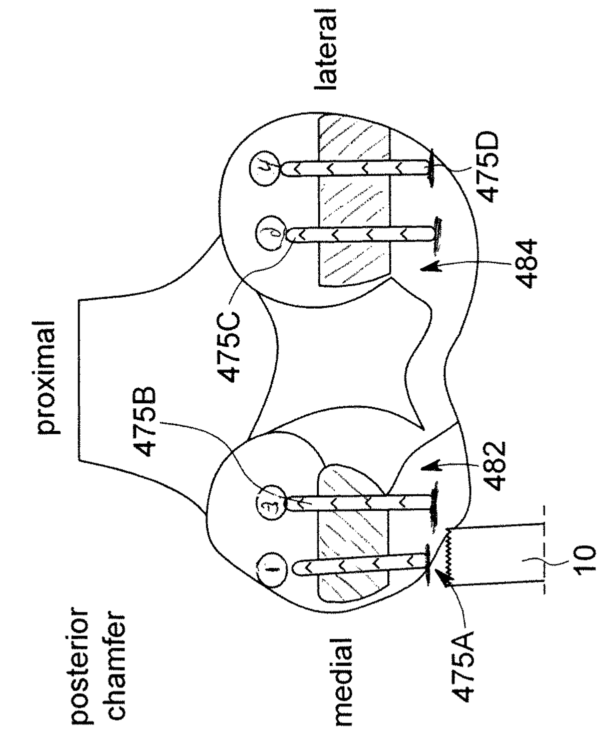
FIGS. 8A and 8B illustrate an exemplary fourth series of programmed sagittal cut paths of the active robotic system of FIG. 3 for forming the TKA resection of FIG. 1, in accordance with one or more aspects of the present disclosure.
Figure 8A:
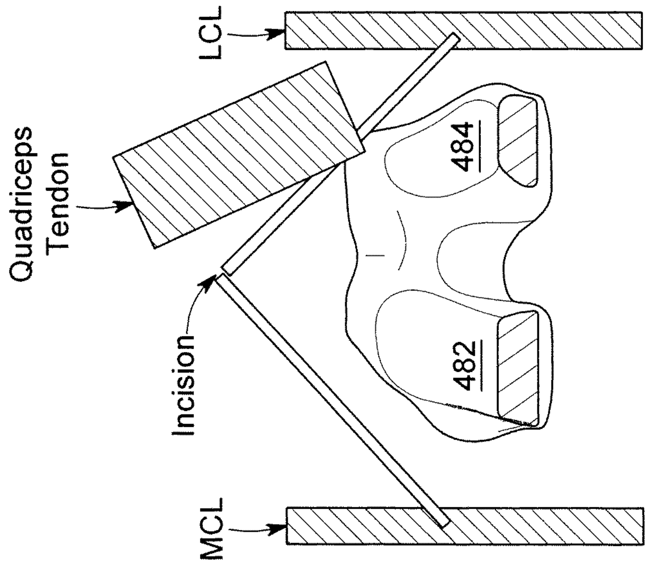

With reference to FIGS. 1, 8A and 8B, the optimized determined, prescribed or programmed cut paths of the sagittal cutting blade 10 of the active/autonomous TKA surgical robotic system 10 and related methods of the present disclosure comprise optimized programmed cut paths 475 configured to create the posterior chamfer resection (between the posterior femur resected surface and the distal femur resected surface), as described above. As shown in FIGS. 1 and 8A, the programmed cut paths 475 for creating the posterior chamfer resection are configured to avoid cutting or otherwise injuring/damaging the patient's quadriceps tendon, MCL, and LCL. As shown in FIGS. 8A and 8B, the cut paths 475 are configured to enter the joint space and engage the medial and lateral condyles from the distal side, and the trajectories of the cut paths 475 extends therethrough distal to proximal.

As shown in FIGS. 8A and 8B, the optimized programmed cut paths 475 of the sagittal cutting blade 10 of the active/autonomous TKA surgical robotic system 10 and related method for creating the posterior chamfer resection comprise cut paths 475 through portions of the medial condyle 482 and the lateral condyle 484. As shown in FIG. 8B, the optimized programmed cut paths 475 of the sagittal cutting blade 10 through the medial condyle 482 for posterior chamfer resection may comprise a first clockwise linear trajectory (distal to proximal) cut path 475A through the medial side of the medial condyle 482 that extends substantially linearly along the medial bone boundary, and a second counterclockwise linear trajectory (distal to proximal) cut path 475B through the lateral side of the medial condyle 482 that extends substantially linearly along the lateral bone boundary.

As also shown in FIG. 8B, the optimized programmed cut paths 475 of the sagittal cutting blade 10 through the lateral condyle 484 for the posterior chamfer resection may comprise a third clockwise trajectory (proximal to distal) cut path 475C through the medial side of the lateral condyle 484 that extends substantially linearly along the medial bone boundary, and a fourth generally counterclockwise linear trajectory (distal to proximal) cut path 475D through the lateral side of the lateral condyle 484 that extends substantially linearly along the lateral bone boundary.

Figure 9B:
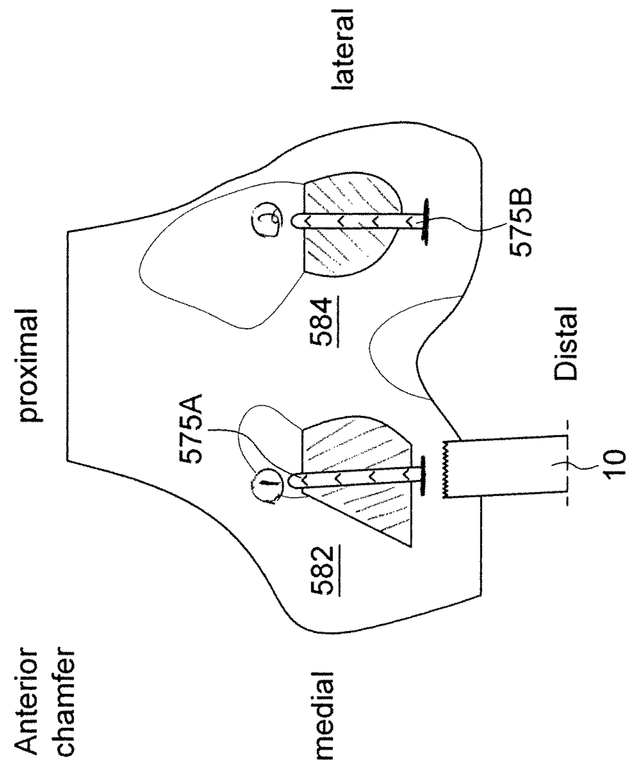
FIGS. 9A and 9B illustrate an exemplary fifth series of programmed sagittal cut paths of the active robotic system of FIG. 3 for forming the TKA resection of FIG. 1, in accordance with one or more aspects of the present disclosure.
Figure 9A:
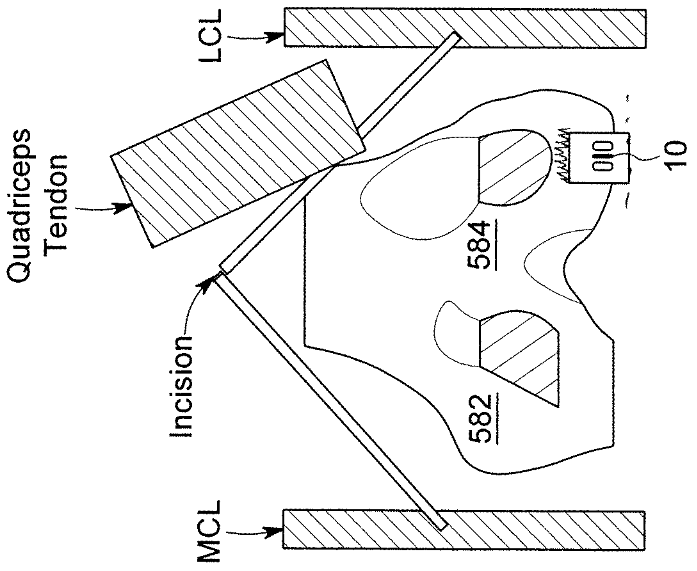

With reference to FIGS. 1, 9A and 9B, the optimized determined, prescribed or programmed cut paths of the sagittal cutting blade 10 of the active/autonomous TKA surgical robotic system 10 and related methods of the present disclosure comprise optimized programmed cut paths 575 configured to create the anterior chamfer resection (between the anterior femur resected surface and the distal femur resected surface), as described above. As shown in FIGS. 1 and 9A, the programmed cut paths 575 for creating the anterior chamfer resection are configured to avoid cutting or otherwise injuring/damaging the patient's quadriceps tendon, MCL, and LCL. As shown in FIGS. 9A and 9B, the cut paths 575 are configured to enter the joint space and engage the medial and lateral condyles from the distal side, and the trajectories of the cut paths 575 extends therethrough distal to proximal.

As shown in FIGS. 9A and 9B, the optimized programmed cut paths 575 of the sagittal cutting blade 10 of the active/autonomous TKA surgical robotic system 10 and related method for creating the anterior chamfer resection comprise cut paths 575 through portions of the medial condyle 582 and the lateral condyle 584. As shown in FIG. 9B, the optimized programmed cut paths 575 of the sagittal cutting blade 10 through the medial condyle 582 for the anterior chamfer resection may comprise a first substantially linear distal to proximal trajectory cut path 575A. In some embodiments, the first cut path 575A may be the only cut necessary to create the anterior chamfer resection on the medial condyle 582, although other linear/ray cut paths may be utilized if necessary.

As also shown in FIG. 9B, the optimized programmed cut paths 575 of the sagittal cutting blade 10 through the lateral condyle 584 for the anterior chamfer resection may comprise a second substantially linear distal to proximal trajectory cut path 575B. In some embodiments, the second cut path 575A may be the only cut necessary to create the anterior chamfer resection on the lateral condyle 584, although other linear/ray cut paths may be utilized if necessary.

Figure 10A:
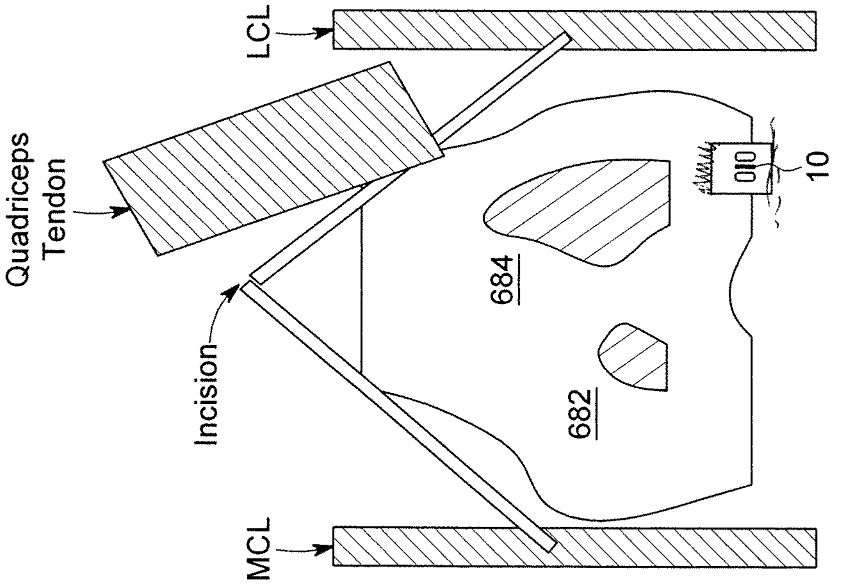
FIGS. 10A and 10B illustrate an exemplary sixth series of programmed sagittal cut paths of the active robotic system of FIG. 3 for forming the TKA resection of FIG. 1, in accordance with one or more aspects of the present disclosure.
Figure 10B:
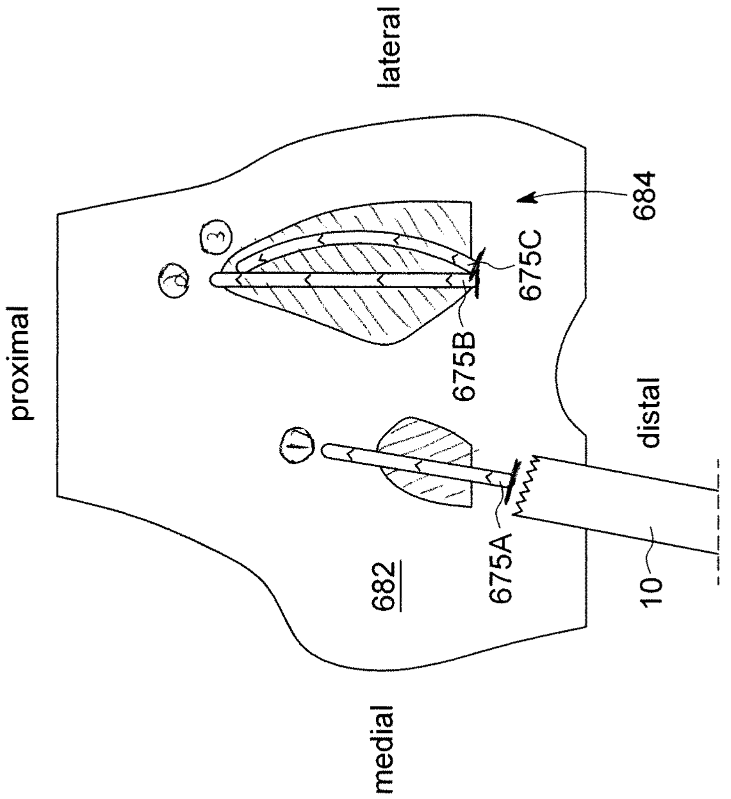

With reference to FIGS. 1, 10A and 10B, the optimized determined, prescribed or programmed cut paths of the sagittal cutting blade 10 of the active/autonomous TKA surgical robotic system 10 and related methods of the present disclosure comprise optimized programmed cut paths 675 configured to create the anterior femur resection through the anterior femur, as described above. As shown in FIGS. 1 and 10A, the programmed cut paths 575 for creating the anterior femur resection are configured to avoid cutting or otherwise injuring/damaging the patient's quadriceps tendon, MCL, and LCL. As shown in FIGS. 10A and 10B, the cut paths 675 are configured to enter the joint space and engage the medial and lateral condyles from the distal side, and the trajectories of the cut paths 675 extends therethrough distal to proximal.

As shown in FIGS. 10A and 10B, the optimized programmed cut paths 675 of the sagittal cutting blade 10 of the active/autonomous TKA surgical robotic system 10 and related method for creating the anterior femur resection comprise cut paths 675 through portions of the medial condyle 682 and the lateral condyle 684. As shown in FIG. 10B, the optimized programmed cut paths 675 of the sagittal cutting blade 10 through the medial condyle 682 for the anterior femur resection may comprise a first substantially linear distal to proximal trajectory cut path 675A. In some embodiments, the first cut path 675A may be the only cut necessary to create the anterior femur resection on the medial condyle 682, although other linear/ray cut paths may be utilized if necessary.

As also shown in FIG. 10B, the optimized programmed cut paths 675 of the sagittal cutting blade 10 through the lateral condyle 684 for the anterior femur resection may comprise a second clockwise linear (distal to proximal) trajectory cut path 675B that extends through the medial side of the lateral condyle 684 substantially linearly along the medial bone boundary, and a third counterclockwise (proximal to distal) trajectory cut path 675C that extends through the lateral side of the lateral condyle 684 arcuately along the lateral bone boundary.

It is to be understood that the above description is intended to be illustrative, and not restrictive. For example, the above-described exemplary embodiments, and/or aspects thereof, may be used in combination with each other. In addition, many modifications may be made to adapt a particular configuration according to the teachings of the various examples without departing from their scope. For example, it is expressly disclosed that the order of the cut paths may be altered, and/or the order of resections may be completed in any order.

Further, the specific configuration of the cut paths and operation of the active surgical robotic systems and methods may be varied without departing from the spirit and scope of the present disclosure. For example, similar cut paths may be utilized with other knee resections, and/or with resections of bones other than the proximal tibia and the distal femur without departing from the spirit and scope of the present disclosure.

Processes described herein may be performed singly or collectively by one or more computer systems, such as one or more systems that are, or are in communication with, the robotic system, such as the articulating joints, end effector, controller, camera system, tracking system, and/or AR system thereof, as examples. FIG. 11 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by Intel Corporation (Santa Clara, California, USA) or ARM Holdings plc (Cambridge, England, United Kingdom), as examples.

FIG. 11 shows a computer system 700 in communication with external device(s) 712. Computer system 700 includes one or more processor(s) 702, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 702 can also include register(s) to be used by one or more of the functional components. Computer system 700 also includes memory 704, input/output (I/O) devices 708, and I/O interfaces 710, which may be coupled to processor(s) 702 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 704 can be or include main or system memory (e.g., Random Access Memory) used in the execution of program instructions, storage device(s) such as hard drive(s), flash media, or optical media as examples, and/or cache memory, as examples. Memory 704 can include, for instance, a cache, such as a shared cache, which may be coupled to local caches (examples include L1 cache, L2 cache, etc.) of processor(s) 702. Additionally, memory 704 may be or include at least one computer program product having a set (e.g., at least one) of program modules, instructions, code or the like that is/are configured to carry out functions of embodiments described herein when executed by one or more processors.

Memory 704 can store an operating system 705 and other computer programs 706, such as one or more computer programs/applications that execute to perform aspects described herein. Specifically, programs/applications can include computer readable program instructions that may be configured to carry out functions of embodiments of aspects described herein.

Examples of I/O devices 708 include but are not limited to microphones, speakers, Global Positioning System (GPS) devices, RGB and/or IR cameras, lights, accelerometers, gyroscopes, magnetometers, sensor devices configured to sense light, proximity, heart rate, body and/or ambient temperature, blood pressure, and/or skin resistance, registration probes and activity monitors. An I/O device may be incorporated into the computer system as shown, though in some embodiments an I/O device may be regarded as an external device (212) coupled to the computer system through one or more I/O interfaces 710.

Computer system 700 may communicate with one or more external devices 712 via one or more I/O interfaces 710. Example external devices include a keyboard, a pointing device, a display, and/or any other devices that enable a user to interact with computer system 700. Other example external devices include any device that enables computer system 700 to communicate with one or more other computing systems or peripheral devices such as a printer. A network interface/adapter is an example I/O interface that enables computer system 700 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Washington, U.S.A.).

The communication between I/O interfaces 710 and external devices 712 can occur across wired and/or wireless communications link(s) 711, such as Ethernet-based wired or wireless connections. Example wireless connections include cellular, Wi-Fi, Bluetooth®, proximity-based, near-field, or other types of wireless connections. More generally, communications link(s) 711 may be any appropriate wireless and/or wired communication link(s) for communicating data.

Particular external device(s) 712 may include one or more data storage devices, which may store one or more programs, one or more computer readable program instructions, and/or data, etc. Computer system 700 may include and/or be coupled to and in communication with (e.g., as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 700 may be operational with numerous other general purpose or special purpose computing system environments or configurations. Computer system 700 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

Various input devices may be provided, such as a camera, which can be used to capture images or video. The camera can be used by the device to obtain image(s)/video of a view of the material to be cut and/or the cutting tool, for instance, capturing images/videos of a scene.

One or more microphones, proximity sensors, light sensors, accelerometers, speakers, GPS devices, and/or other input devices (not labeled) may be additionally provided. Electronic components, such as electronic circuitry, including processor(s), memory, and/or communications devices, such as cellular, short-range wireless (e.g., Bluetooth), or Wi-Fi circuitry for connection to remote devices may be included. A power source, such as a battery to power components of the system may also be incorporated. Physical port(s) (not pictured) used to connect device the computer to a power source (to recharge a battery) and/or any other external device, such as the controller. Such physical ports can be of any standardized or proprietary type, such as Universal Serial Bus (USB).

Aspects of the present invention may be a system, a method, and/or a computer program product, any of which may be configured to perform or facilitate aspects described herein.

In some embodiments, aspects of the present invention may take the form of a computer program product, which may be embodied as computer readable medium(s). A computer readable medium may be a tangible storage device/medium having computer readable program code/instructions stored thereon. Example computer readable medium(s) include, but are not limited to, electronic, magnetic, optical, or semiconductor storage devices or systems, or any combination of the foregoing. Example embodiments of a computer readable medium include a hard drive or other mass-storage device, an electrical connection having wires, random access memory (RAM), read-only memory (ROM), erasable-programmable read-only memory such as EPROM or flash memory, an optical fiber, a portable computer disk/diskette, such as a compact disc read-only memory (CD-ROM) or Digital Versatile Disc (DVD), an optical storage device, a magnetic storage device, or any combination of the foregoing. The computer readable medium may be readable by a processor, processing unit, or the like, to obtain data (e.g., instructions) from the medium for execution. In a particular example, a computer program product is or includes one or more computer readable media that includes/stores computer readable program code to provide and facilitate one or more aspects described herein.

As noted, program instruction contained or stored in/on a computer readable medium can be obtained and executed by any of various suitable components such as a processor of a computer system to cause the computer system to behave and function in a particular manner. Such program instructions for carrying out operations to perform, achieve, or facilitate aspects described herein may be written in, or compiled from code written in, any desired programming language. In some embodiments, such programming language includes object-oriented and/or procedural programming languages such as C, C++, C#, Java, etc.

Program code can include one or more program instructions obtained for execution by one or more processors. Computer program instructions may be provided to one or more processors of, e.g., one or more computer systems, to produce a machine, such that the program instructions, when executed by the one or more processors, perform, achieve, or facilitate aspects of the present invention, such as actions or functions described in flowcharts and/or block diagrams described herein. Thus, each block, or combinations of blocks, of the flowchart illustrations and/or block diagrams depicted and described herein can be implemented, in some embodiments, by computer program instructions.

Many other examples will be apparent to those of skill in the art upon reviewing the above description. The scope of the various examples should, therefore, be determined with reference to the appended claims, along with the full scope of equivalents to which such claims are entitled.

While dimensions and types of materials may be described herein, they are intended to define parameters of some of the various examples, and they are by no means limiting to all examples and are merely exemplary.

In the appended claims, the terms "including" and "in which" are used as the plain-English equivalents of the respective terms "comprising" and "wherein." Moreover, in the following claims, the terms "first," "second," and "third," etc. are used merely as referee labels, and are not intended to impose numerical, structural or other requirements on their objects.

Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function cavity of further structure. It is to be understood that not necessarily all such objects or advantages described above may be achieved in accordance with any particular example. Thus, for example, those skilled in the art will recognize that the devices, systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some disclosure are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

We claim:

1. An active robotic system comprising:

an articulated arm comprising a plurality of arm segments defining longitudinal axes, and adjustable joints coupled between adjacent arm segments that are configured to adjust the orientation of the axes of the adjacent arm segments;

a sagittal cutting blade defining a cutting edge that is configured to cut while being oscillated along an oscillation pathway that extends on a plane defined by the blade;

an end effector coupled to an end arm segment of the plurality of arm segments and the sagittal cutting blade, the end effector comprising a powered drive portion that oscillates the sagittal cutting blade along the oscillation pathway; and a computing device communicatively coupled to the articulated arm, the sagittal cutting blade, and the end effector, wherein the computing device includes instructions that, when executed by the computing device, cause the robotic system to autonomously adjust the relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, wherein the plurality of optimized programmed cut paths comprise a first series of cut paths that are configured to create a tibial resection on the proximal tibia while preventing injury to the patient's patellar tendon, medial collateral ligament (MCL), lateral collateral ligament (LCL), and posterior cruciate ligament (PCL), wherein the first series of cut paths are configured to enter a joint space between the patient's proximal tibia and the distal femur via an entry region on an anterior-medial bone region, and trajectories of the cut paths of the first series of cut paths extend between the patient's MCL and patellar tendon, wherein the first series of cut paths comprise a first counterclockwise anterior to posterior trajectory cut path that arcuately extends along a lateral bone boundary of the proximal tibia, and a second anterior to posterior clockwise trajectory cut path that arcuately extends along a medial bone boundary of the proximal tibia, wherein the first series of cut paths further comprise at least one third cut path that extends between the first and second cut paths of the first series of cut paths to remove portions of the proximal tibia that extend between the first and second cut paths to form the tibial resection, and wherein the plurality of optimized programmed cut paths comprise a second series of cut paths that are configured to create distal femur resections on medial and lateral condyles of the distal femur while preventing injury to the patient's quadriceps tendon, MCL, popliteal tendon, and LCL.

2. The robotic system of claim 1, wherein the second series of cut paths are configured to enter the joint space between the patient's proximal tibia and the distal femur via an entry region on an anterior side of the posterior femur, and the trajectories of the cut paths of the second series of cut paths extend therethrough in an anterior to posterior direction.

3. The robotic system of claim 2, wherein the second series of cut paths comprises a first subseries of cut paths extending through a portion of the medial condyle of the distal femur, and wherein the first subseries of cut paths comprises a first counterclockwise anterior to posterior trajectory cut path through a medial side of the medial condyle that arcuately extends along a medial bone boundary of the distal femur, and a second clockwise anterior to posterior trajectory cut path through a lateral side of the medial condyle that arcuately extends along a lateral bone boundary of the distal femur.

4. The robotic system of claim 3, wherein the first subseries of cut paths further comprises at least one third cut path trajectory that extends anterior to posterior and between the first and second cut paths of the first subseries of cut paths to remove portions of the distal femur that extend between the first and second cut paths to form distal femur resection on medial condyle.

5. The robotic system of claim 4, wherein the second series of cut paths comprises a second subseries of cut paths extending through a portion of the lateral condyle of the distal femur, and wherein the second subseries of cut paths comprises a third counterclockwise anterior to posterior trajectory cut path through a medial side of the lateral condyle of the distal femur that arcuately extends along a medial bone boundary of the distal femur, and a fourth generally clockwise anterior to posterior trajectory cut path through a lateral side of the lateral condyle of the distal femur that extends along a lateral bone boundary of the distal femur.

6. The robotic system of claim 5, wherein the plurality of optimized programmed cut paths comprise a third series of cut paths that are configured to create posterior femur resections on medial and lateral condyles of the posterior femur while preventing injury to the patient's quadriceps tendon, MCL, popliteal tendon, and LCL.

7. The robotic system of claim 6, wherein the third series of cut paths are configured to enter the joint space between the patient's proximal tibia and the distal femur via an entry region on the distal side of the posterior femur, and the trajectories of the cut paths of the third series of cut paths extend therethrough in a distal to proximal direction.

8. The robotic system of claim 7, wherein the third series of cut paths comprises a third subseries of cut paths extending through a portion of the medial condyle of the posterior femur, and wherein the third subseries of cut paths comprises a first clockwise distal to proximal substantially linear trajectory cut path through a medial side of the medial condyle that extends substantially linearly along a medial bone boundary of the posterior femur, and a second counterclockwise distal to proximal substantially linear trajectory cut path through a lateral side of the medial condyle that extends substantially linearly along a lateral bone boundary of the posterior femur.

9. The robotic system of claim 8, wherein the third series of cut paths comprises a fourth subseries of cut paths extending through a portion of the lateral condyle of the posterior femur, and wherein the fourth subseries of cut paths comprises a third clockwise proximal to distal trajectory cut path through a medial side of the lateral condyle of the posterior femur that extends substantially linearly along a medial bone boundary of the posterior femur, and a fourth generally counterclockwise distal to proximal substantially linear trajectory cut path through a lateral side of the lateral condyle of the posterior femur that extends substantially linearly along a lateral bone boundary of the posterior femur.

10. The robotic system of claim 9, wherein the plurality of optimized programmed cut paths comprise a fourth series of cut paths that are configured to create posterior chamfer resection on medial and lateral condyles of the femur that extend between the posterior-distal femur while preventing injury to the patient's quadriceps tendon, MCL, and LCL.

11. The robotic system of claim 10, wherein the fourth series of cut paths are configured to enter the joint space between the patient's proximal tibia and the distal femur via an entry region on the distal side of the posterior-distal femur, and the trajectories of the cut paths of the fourth series of cut paths extend therethrough in a distal to proximal direction.

12. The robotic system of claim 11, wherein the fourth series of cut paths comprises a fifth subseries of cut paths extending through a portion of the medial condyle of the posterior-distal femur, and wherein the fifth subseries of cut paths comprises a first clockwise distal to proximal substantially linear trajectory cut path through a medial side of the medial condyle that extends substantially linearly along a medial bone boundary of the posterior-distal femur, and a second counterclockwise distal to proximal substantially linear trajectory cut path through a lateral side of the medial condyle that extends substantially linearly along a lateral bone boundary of the posterior-distal femur.

13. The robotic system of claim 12, wherein the fourth series of cut paths comprises a sixth subseries of cut paths extending through a portion of the lateral condyle of the posterior-distal femur, and wherein the fourth subseries of cut paths comprises a third clockwise proximal to distal trajectory cut path through a medial side of the lateral condyle of the posterior-distal femur that extends substantially linearly along a medial bone boundary of the posterior-distal femur, and a fourth generally counterclockwise distal to proximal substantially linear trajectory cut path through a lateral side of the lateral condyle of the posterior-distal femur that extends substantially linearly along a lateral bone boundary of the posterior-distal femur.

14. The robotic system of claim 13, wherein the plurality of optimized programmed cut paths comprise a fifth series of cut paths that are configured to create anterior chamfer resection on medial and lateral condyles of the femur that extend between the anterior-distal femur while preventing injury to the patient's quadriceps tendon, MCL, and LCL.

15. The robotic system of claim 14, wherein the fifth series of cut paths are configured to enter the joint space between the patient's proximal tibia and the distal femur via an entry region on the distal side of the anterior-distal femur, and the trajectories of the cut paths of the fifth series of cut paths extend therethrough in a distal to proximal direction.

16. The robotic system of claim 15, wherein the fifth series of cut paths comprises a seventh subseries of cut paths extending through a portion of the medial condyle of the anterior-distal femur, and wherein the seventh subseries of cut paths comprises a first distal to proximal substantially linear trajectory cut path through the medial condyle.

17. The robotic system of claim 16, wherein the fifth series of cut paths comprises an eighth subseries of cut paths extending through a portion of the lateral condyle of the anterior-distal femur, and wherein the eighth subseries of cut paths comprises a second distal to proximal substantially linear trajectory cut path through the lateral condyle.

18. The robotic system of claim 17, wherein the plurality of optimized programmed cut paths comprise a sixth series of cut paths that are configured to create anterior femur resections on medial and lateral condyles of the anterior femur while preventing injury to the patient's quadriceps tendon, MCL, popliteal tendon and LCL.

19. The robotic system of claim 18, wherein the sixth series of cut paths are configured to enter the joint space between the patient's proximal tibia and the distal femur via an entry region on the distal side of the anterior femur, and the trajectories of the cut paths of the sixth series of cut paths extend therethrough in a distal to proximal direction.

20. The robotic system of claim 19, wherein the sixth series of cut paths comprises a ninth subseries of cut paths extending through a portion of the medial condyle of the anterior femur, and wherein the ninth subseries of cut paths comprises a first substantially linear distal to proximal trajectory cut path through the medial condyle.

21. The robotic system of claim 20, wherein the sixth series of cut paths comprises a tenth subseries of cut paths extending through a portion of the lateral condyle of the anterior femur, and wherein the tenth subseries of cut paths comprises a second clockwise substantially linear distal to proximal trajectory cut path through the medial side of the lateral condyle extending substantially linearly along a medial bone boundary of the anterior femur, and a third counterclockwise proximal to distal trajectory cut path through the lateral side of the lateral condyle extending arcuately along a lateral bone boundary of the anterior femur.

22. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise at least two series of cuts comprising:

a first series of cut paths that are configured to create a tibial resection on the proximal tibia while preventing injury to the patient's patellar tendon, medial collateral ligament (MCL), lateral collateral ligament (LCL), and posterior cruciate ligament (PCL);

a second series of cut paths that are configured to create distal femur resections on medial and lateral condyles of the distal femur while preventing injury to the patient's quadriceps tendon, MCL, popliteal tendon, and LCL;

a third series of cut paths that are configured to create posterior femur resections on medial and lateral condyles of the posterior femur while preventing injury to the patient's quadriceps tendon, MCL, popliteal tendon, and LCL;

a fourth series of cut paths that are configured to create posterior chamfer resection on medial and lateral condyles of the femur that extend between the posterior-distal femur while preventing injury to the patient's quadriceps tendon, MCL, and LCL;

a fifth series of cut paths that are configured to create anterior chamfer resection on medial and lateral condyles of the femur that extend between the anterior-distal femur while preventing injury to the patient's quadriceps tendon, MCL, and LCL; and a sixth series of cut paths that are configured to create anterior femur resections on medial and lateral condyles of the anterior femur while preventing injury to the patient's quadriceps tendon, MCL, popliteal tendon and LCL.

23. The robotic system of claim 22, wherein the plurality of optimized programmed cut paths comprise at least three series of cuts comprising the first, second, third, fourth, fifth and sixth series of cut paths.

24. The robotic system of claim 22, wherein the plurality of optimized programmed cut paths comprise at least four series of cuts comprising the first, second, third, fourth, fifth and sixth series of cut paths.

25. The robotic system of claim 22, wherein the plurality of optimized programmed cut paths comprise at least five series of cuts comprising the first, second, third, fourth, fifth and sixth series of cut paths.

26. The robotic system of claim 22, wherein the plurality of optimized programmed cut paths comprises each of the first, second, third, fourth, fifth and sixth series of cut paths.

27. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise a series of cut paths that are configured to create distal femur resections on medial and lateral condyles of the distal femur while preventing injury to the patient's quadriceps tendon, MCL, popliteal tendon, and LCL.

28. The robotic system of claim 27, wherein the series of cut paths are configured to enter a joint space between the patient's proximal tibia and the distal femur via an entry region on the anterior side of the posterior femur, and the trajectories of the cut paths of the series of cut paths extend therethrough in an anterior to posterior direction.

29. The robotic system of claim 27, wherein the series of cut paths comprises a first subseries of cut paths extending through a portion of the medial condyle of the distal femur, and wherein the first subseries of cut paths comprises a first counterclockwise anterior to posterior trajectory cut path through a medial side of the medial condyle that arcuately extends along a medial bone boundary of the distal femur, and a second clockwise anterior to posterior trajectory cut path through a lateral side of the medial condyle that arcuately extends along a lateral bone boundary of the distal femur.

30. The robotic system of claim 29, wherein the first subseries of cut paths further comprises at least one third cut path trajectory that extends anterior to posterior and between the first and second cut paths of the first subseries of cut paths to remove portions of the distal femur that extend between the first and second cut paths to form distal femur resection on medial condyle.

31. The robotic system of claim 27, wherein the series of cut paths comprises a subseries of cut paths extending through a portion of the lateral condyle of the distal femur, and wherein the subseries of cut paths comprises a counterclockwise anterior to posterior trajectory cut path through a medial side of the lateral condyle of the distal femur that arcuately extends along a medial bone boundary of the distal femur, and a generally clockwise anterior to posterior trajectory cut path through a lateral side of the lateral condyle of the distal femur that extends along a lateral bone boundary of the distal femur.

32. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise a series of cut paths that are configured to create posterior femur resections on medial and lateral condyles of the posterior femur while preventing injury to the patient's quadriceps tendon, MCL, popliteal tendon, and LCL.

33. The robotic system of claim 32, wherein the series of cut paths are configured to enter a joint space between the patient's proximal tibia and the distal femur via an entry region on the distal side of the posterior femur, and trajectories of the cut paths of the series of cut paths extend therethrough in a distal to proximal direction.

34. The robotic system of claim 32, wherein the series of cut paths comprises a subseries of cut paths extending through a portion of the medial condyle of the posterior femur, and wherein the subseries of cut paths comprises a first clockwise distal to proximal substantially linear trajectory cut path through a medial side of the medial condyle that extends substantially linearly along a medial bone boundary of the posterior femur, and a second counterclockwise distal to proximal substantially linear trajectory cut path through a lateral side of the medial condyle that extends substantially linearly along a lateral bone boundary of the posterior femur.

35. The robotic system of claim 32, wherein the series of cut paths comprises a subseries of cut paths extending through a portion of the lateral condyle of the posterior femur, and wherein the subseries of cut paths comprises a clockwise proximal to distal trajectory cut path through a medial side of the lateral condyle of the posterior femur that extends substantially linearly along a medial bone boundary of the posterior femur, and a generally counterclockwise distal to proximal substantially linear trajectory cut path through a lateral side of the lateral condyle of the posterior femur that extends substantially linearly along a lateral bone boundary of the posterior femur.

36. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise a series of cut paths that are configured to create posterior chamfer resection on medial and lateral condyles of the femur that extend between the posterior-distal femur while preventing injury to the patient's quadriceps tendon, MCL, and LCL.

37. The robotic system of claim 36, wherein the series of cut paths are configured to enter a joint space between the patient's proximal tibia and the distal femur via an entry region on the distal side of the posterior-distal femur, and trajectories of the cut paths of the series of cut paths extend therethrough in a distal to proximal direction.

38. The robotic system of claim 36, wherein the series of cut paths comprises a subseries of cut paths extending through a portion of the medial condyle of the posterior-distal femur, and wherein the subseries of cut paths comprises a first clockwise distal to proximal substantially linear trajectory cut path through a medial side of the medial condyle that extends substantially linearly along a medial bone boundary of the posterior-distal femur, and a second counterclockwise distal to proximal substantially linear trajectory cut path through a lateral side of the medial condyle that extends substantially linearly along a lateral bone boundary of the posterior-distal femur.

39. The robotic system of claim 36, wherein the series of cut paths comprises a subseries of cut paths extending through a portion of the lateral condyle of the posterior-distal femur, and wherein the subseries of cut paths comprises a clockwise proximal to distal trajectory cut path through a medial side of the lateral condyle of the posterior-distal femur that extends substantially linearly along a medial bone boundary of the posterior-distal femur, and a generally counterclockwise distal to proximal substantially linear trajectory cut path through a lateral side of the lateral condyle of the posterior-distal femur that extends substantially linearly along a lateral bone boundary of the posterior-distal femur.

40. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise a series of cut paths that are configured to create anterior chamfer resection on medial and lateral condyles of the femur that extend between the anterior-distal femur while preventing injury to the patient's quadriceps tendon, MCL, and LCL.

41. The robotic system of claim 40, wherein the series of cut paths are configured to enter a joint space between the patient's proximal tibia and the distal femur via an entry region on the distal side of the anterior-distal femur, and trajectories of the cut paths of the fifth series of cut paths extend therethrough in a distal to proximal direction.

42. The robotic system of claim 40, wherein the series of cut paths comprises a subseries of cut paths extending through a portion of the medial condyle of the anterior-distal femur, and wherein the subseries of cut paths comprises a first distal to proximal substantially linear trajectory cut path through the medial condyle.

43. The robotic system of claim 40, wherein the series of cut paths comprises an subseries of cut paths extending through a portion of the lateral condyle of the anterior-distal femur, and wherein the subseries of cut paths comprises a distal to proximal substantially linear trajectory cut path through the lateral condyle.

44. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths comprise a series of cut paths that are configured to create anterior femur resections on medial and lateral condyles of the anterior femur while preventing injury to the patient's quadriceps tendon, MCL, popliteal tendon and LCL.

45. The robotic system of claim 44, wherein the series of cut paths are configured to enter a joint space between the patient's proximal tibia and the distal femur via an entry region on the distal side of the anterior femur, and trajectories of the cut paths of the series of cut paths extend therethrough in a distal to proximal direction.

46. The robotic system of claim 44, wherein the series of cut paths comprises a subseries of cut paths extending through a portion of the medial condyle of the anterior femur, and wherein the subseries of cut paths comprises a first substantially linear distal to proximal trajectory cut path through the medial condyle.

47. The robotic system of claim 44, wherein the series of cut paths comprises a subseries of cut paths extending through a portion of the lateral condyle of the anterior femur, and wherein the subseries of cut paths comprises a clockwise substantially linear distal to proximal trajectory cut path through the medial side of the lateral condyle extending substantially linearly along a medial bone boundary of the anterior femur, and a counterclockwise proximal to distal trajectory cut path through the lateral side of the lateral condyle extending arcuately along a lateral bone boundary of the anterior femur.

48. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the plurality of optimized programmed cut paths are programmed in memory of the robotic system.

49. The robotic system of claim 48, wherein the robotic system is configured to autonomously execute the plurality of optimized programmed cut paths via the sagittal cutting blade without a user physically guiding the sagittal cutting blade.

50. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the robotic system is configured to autonomously spatially translate the cutting edge of the sagittal cutting blade continuously along a respective cut path.

51. A robotic system comprising:

an articulated arm comprising a plurality of arm segments defining longitudinal axes, and adjustable joints coupled between adjacent arm segments that are configured to adjust an orientation of the axes of the adjacent arm segments;

a sagittal cutting blade defining a cutting edge that is configured to cut while being oscillated along an oscillation pathway that extends on a plane defined by the blade; and an end effector coupled to an end arm segment of the plurality of arm segments and the sagittal cutting blade, the end effector comprising a powered drive portion that oscillates the sagittal cutting blade along the oscillation pathway, wherein the robotic system is configured to autonomously adjust a relative orientation of the arm segments of the articulated arm while the sagittal cutting blade oscillates along the cutting pathway to autonomously spatially translate the cutting edge of the sagittal cutting blade along a plurality of optimized programmed cut paths to perform resections of portions of a proximal tibia and/or a distal femur of a patient via the sagittal cutting blade to facilitate implantation of a femoral component and a tibial component, respectively, of a total knee arthroplasty prosthesis thereon, and wherein the robotic system is configured to autonomously spatially translate the cutting edge of the sagittal cutting blade along a series of different paths that collectively extend along a respective cut path.

* * * * *